United States Patent [19]
Thompson et al.

[11] Patent Number: 5,645,531
[45] Date of Patent: Jul. 8, 1997

[54] CONSTANT PRESSURE BLOOD MIXTURE DELIVERY SYSTEM AND METHOD

[75] Inventors: Thomas C. Thompson, McKinney; Martyn Abbott, Richardson; Kenneth A. Jones, McKinney, all of Tex.

[73] Assignee: Quest Medical, Inc., Allen, Tex.

[21] Appl. No.: 204,530

[22] Filed: Mar. 1, 1994

Related U.S. Application Data

[63] Continuation-in-part of Ser. No. 67,683, May 26, 1993, Pat. No. 5,385,540.
[51] Int. Cl.$^6$ .................................................. A61M 31/00
[52] U.S. Cl. .................. 604/67; 604/48; 604/65; 128/DIG. 3
[58] Field of Search .................... 604/4, 27–29, 604/65–67, 131, 151, 153, 48; 128/DIG. 3, DIG. 12

[56] References Cited

U.S. PATENT DOCUMENTS

| | | | |
|---|---|---|---|
| T994,001 | 5/1980 | Buckberg et al. | 128/214 R |
| 4,236,880 | 12/1980 | Archibald | 417/478 |
| 4,401,431 | 8/1983 | Arp | 604/4 |
| 4,416,280 | 11/1983 | Carpenter et al. | 128/399 |
| 4,464,172 | 8/1984 | Lichtenstein | 604/65 |
| 4,466,804 | 8/1984 | Hino | 604/4 |
| 4,479,761 | 10/1984 | Bilstad et al. | |
| 4,529,397 | 7/1985 | Hennemuth et al. | 604/4 |
| 4,568,330 | 2/1986 | Kujawski et al. | 604/53 |
| 4,657,490 | 4/1987 | Abbott | 417/478 |
| 4,696,671 | 9/1987 | Epstein et al. | 604/67 |
| 4,821,761 | 4/1989 | Aid et al. | 137/101.21 |
| 4,828,543 | 5/1989 | Weiss et al. | 604/4 |
| 4,874,359 | 10/1989 | White et al. | 604/4 |
| 4,883,455 | 11/1989 | Leonard | 604/4 |
| 5,171,212 | 12/1992 | Buck et al. | 604/4 |
| 5,307,288 | 4/1994 | Haines | 364/510 |

OTHER PUBLICATIONS

Eliot R. Rosenkrantz, M.D., et al., "Warm Induction of Cardioplegia with Glutamate–Enriched Blood in Coronary Patients with Cardiogenic Shock Who Are Dependent on Inotropic Drugs and Intra–Aortic Balloon Support," *The Journal of Thoracic and Cardiovascular Surgery* (1983) 86, pp. 507–518.

Philippe Menasche, M.D., et al., "Retrograde Coronary Sinus Perfusion: A Safe Alternative for Ensuring Cardioplegic Delivery in Aortic Valve Surgery," *The Annals of Thoracic Surgery*, vol. 34, No. 6 (Dec. 1982), pp. 647–658.

Eliot R. Rosenkranz, M.D., et al., "Myocardial Protection During Surgical Coronary Reperfusion," *The American College of Cardiology* (1983), pp. 1235–1246.

Eliot R. Rosenkranz, M.D., et al., "Benefits of Normothermic Induction of Blood Cardioplegia in Energy Depleted Hearts, with Maintenance of Arrest by Multidose Cold Blood Cardioplegic Infusions," *The Journal of Thoracic and Cardiovascular Surgery*, vol. 84, No. 5 (Nov., 1982), pp. 667–677.

John M. Robertson, M.D., et al., "Comparison of Distribution Beyond Coronary Stenoses of Blood and Asanguineous Cardioplegic Solutions," *The Journal of Thoracic and Cardiovascular Surgery*, vol. 1, No. 1 (Jul. 1983), pp. 80–86.

(List continued on next page.)

*Primary Examiner*—Corrine M. McDermott
*Attorney, Agent, or Firm*—John W. Montgomery

[57] ABSTRACT

A system and method for blood mixture fluid delivery to a patient includes fluid delivery conduits connected to the patient for delivering blood mixture fluid, a pump for controlled pumping of blood mixture fluid through the conduits to the patient, and an automatic control mechanism operatively connected to the pump for controlling the pump so that the blood mixture fluid is continuously delivered to the patient at a defined constant pressure.

29 Claims, 7 Drawing Sheets

OTHER PUBLICATIONS

David M. Follette, M.D., et al., "Advantages of Blood Cardioplegia Over Continuous Coronary Perfusion or Intermittent Ischemia," *The Journal of Thoracic and Cardiovascular Surgery*, vol. 76, No. 5 (Nov. 1978), pp. 604–619.

Arthur J. Roberts, et al., "Clinical Evaluation of the Relative Effectiveness of Multidose Crystalloid and Cold Blood Potassium Cardioplegia in Coronary Artery Bypass Graft Surgery; A Nonrandomized Matched–Pair Analysis," *The Annals of Thoracic Surgery*, vol. 33, No. 5 (May 1982), pp. 421–433.

Daniel Le Houerou, et al., "Minimal Hemodilution and Optimal Potassium Use During Normothermic Aerobic Arrest," *Annual Thoracic Surgery* (1992) 54:809–16, pp. 815–816.

Philippe Menasche, M.D., Ph.D., et al., "Simplified Method for Delivering Normothermic Blood Cardioplegia," *The Society of Thoracic Surgeons* (1993) 55:177–8.

Ad: "Cardioplegic Controller," Stöckert CAPS Cardioplegic Controller (Product Designation 27–60–00), Sorin Biomedical Inc. (two–page advertisement—© 1993).

Valleylab promotional brocheure for the Infutrol 7000. Sep. 1983.

CONSTANT PRESSURE BLOOD MIXTURE DELIVERY SYSTEM AND METHOD

CROSS-REFERENCE TO RELATED APPLICATIONS

This application is a continuation-in-part of co-owned and U.S. patent application Ser. No. 08/067,683 filed May 26, 1993 which issued on Jan. 31, 1995 as U.S. Pat. No. 5,383,540 and is also related to co-owned, co-pending United States Patent Application entitled "Display Panel and Controls for Blood Mixture Delivery System" filed concurrently herewith, on Mar. 1, 1994 as Ser. No. 08/204,532, both of which related applications are incorporated by reference as if fully set forth herein.

TECHNICAL FIELD OF THE INVENTION

This invention relates to fluid delivery systems, and more particularly, the systems for blood mixture fluid delivery to an organ, limb or other body part of a patient during a medical procedure.

BACKGROUND OF THE INVENTION

In the performance of medical procedures, such as open heart surgery, isolated limb reperfusion, cerebral or neuro-perfusion, or the like, the patient may be supported by an extracorporeal blood circuit employing a heart flung machine. Isolated organs or limbs may also be separately supplied with a blood mixture fluid, which may include a portion of the oxygenated blood from such an extracorporeal blood circuit, with or without other constituents. In the specific case of open heart surgery, for example, the heart is isolated from the vascular system, and venous blood is diverted into the extracorporeal blood circuit where it is oxygenated, temperature-controlled and returned to the patient's arterial side. A separate circuit is established for supplying a blood mixture fluid to the heart as the surgery proceeds. The constituents of such a blood mixture fluid will depend upon the procedure. In some situations, the blood mixture fluid will include whole blood; in other uses, it may be a mixture of blood, plasma and/or platelets or blood mixed with other constituents, agents and or additives. For example, during open heart surgery, a patient's heart may be supplied with a cardioplegia solution to stop the heart. A different blood fluid mixture might be used to maintain the heart during surgery, and another for reperfusion after surgery.

When the blood mixture fluid is a cardioplegia solution, it functions to still the heart, lower the metabolic requirements of the heart, protect the heart during periods of ischemia, and, finally, prepare the heart for reperfusion at the end of the procedure. Operation of the extracorporeal blood circuit as well as the cardioplegia delivery is performed by a trained perfusionist under the direction of the cardiovascular surgeon. The principal elements of advanced cardioplegia solutions are blood, representing a small fraction diverted from the output of the heart/lung machine, combined with a crystalloid solution. The crystalloid solution is a premixed aqueous saline or glucose solution, metabolic substrates to feed the heart tissue, and may also contain buffers, special medications and additives to protect and preserve the heart during periods of ischemia and to prepare the heart for reperfusion with the normal blood supply. In addition, a minor but critical amount of potassium solution is added to the cardioplegic flow to still the heart.

Depending upon the requirements of the particular surgery, the cardioplegia solution may be cooled or warmed, and may be delivered in antegrade fashion to the aortic root or coronary ostia, or in a retrograde mode to the coronary sinus. The mode of delivery and composition of the cardioplegia solution may vary as the surgery proceeds, and are subject to the clinical judgment of the individual surgeon.

A typical cardioplegia delivery system employs two tubes routed through a single rotary peristaltic pump to forward both the separate blood and crystalloid solutions to a Y combining the two into a single flow. The ratio between the blood and crystalloid solution is determined simply by the relative diameters of the tubing carrying the two solutions, since each is mounted on the same rotary peristaltic mechanism and thus is forwarded by the same action. The tubing is usually provided in a 4:1 ratio of blood to crystalloid cross-sectional flow area, so that the rotary peristaltic pump is delivering blood and crystalloid to the delivery line in a ratio of approximately 4:1. Potassium is typically provided to the delivery line upstream of the pump from two alternate crystalloid solutions containing potassium, one having a relatively high concentration of potassium to stop the heart, the other a lower concentration of potassium sufficient to maintain the heart in the arrested state. The surgeon selects between the two sources as monitoring of the patient's condition indicates. The higher potassium concentration is utilized to arrest the heart, while the lower is used to maintain the stilled condition. The clinical team must provide sufficient potassium in the cardioplegia solution to establish the stilled condition of the heart and to maintain it during the procedure, while avoiding the risks associated with hyperkalemia and hemodilution which may result from excessive cardioplegia solution delivery.

Existing systems for delivery of cardioplegia are characterized by poor adaptability to varying requirements which the surgeon in charge may place upon the system as to parameters or characteristics of the cardioplegia fluid, including, for example, flow rate, pressure, ratios of blood to crystalloid, solution additives, temperature, and flow direction through the heart. For example, control of the ratio of blood to crystalloid solutions is not possible with present systems because the ratio is fixed by the size of the tubing routed through the peristaltic pump. Some of these parameters or characteristics have been controlled to a limited extent in prior systems. The control, if any, has been independently effectuated at separate instrumentation which has been interconnected with tubing to form a complete cardioplegia delivery system. The systems have particularly poor control over the cardioplegia delivery at low flow rates. Moreover, the shearing forces to which the blood in the cardioplegia line is subjected by peristaltic pump action risks damage to the blood. Furthermore, existing systems depend primarily on controlling the flow rate through manual adjustments in order to maintain a sufficient pressure to force the cardioplegia fluid through the vascular system of the heart while avoiding excessive pressure which might rupture the vessels or heart tissue. Also, the requirements are different for antegrade perfusion and for retrograde perfusion.

In our co-pending patent application filed on May 26, 1993, Ser. No. 08/067,683, which is incorporated herein by reference as if set forth herein, a cardioplegia system is provided for delivering cardioplegia solutions to a heart during open-heart surgery. The system cooperates with an extra-corporeal blood circuit employing a heart/lung machine. The system includes a conduit for diverting a portion of the blood flow from the heart/lung machine to the cardioplegia delivery line. A heat exchanger controls fluid temperature in the cardioplegia delivery line. A first pump combines blood from the conduit with a second fluid and delivers the combined fluid flow into the delivery line leading into the heat exchanger. A second pump is provided for delivery of a third fluid, typically the arrest agent, into the delivery line downstream from the first pump. The second pump has a flow rate less than about ten percent (10%) of the flow rate of the combined output of the first pump. Control means are included for adjusting the ratio of blood and second fluids which is delivered by the first pump and for adjusting the total volumetric rate of flow from the pump. Preferably, the volumetric flow rate of the first, second and third fluids are maintained at its desired percentage relative to each other. A third pump is provided for delivery of a fourth fluid, typically an additive, in combination with the output of the first and second pumps. Control means are provided for automatically controlling the output of the third pump in proportion to the variable output of the first pump.

In giving cardioplegia solutions for the heart, either for delivering an arrest agent which stops the heart for surgery or other additives which help take care of the heart, it is important to have adequate perfusion of all regions of the heart to ensure adequate preservation of the heart muscle. Delivery of an adequate flow rate does not guarantee that all regions of the heart are adequately perfused. In fact, most users increase the flow rate until an operating pressure is achieved and then attempt to operate at or near the same flow rate so that the pressure is likely to stay within a limited range. It is extremely difficult to control the flow rate in order to keep the pressure relatively constant because it is a continually dynamic system. Furthermore, it is not uncommon for the surgeon to pick up the heart or to move it and cause high resistance at the tip of the cannula, which increases the pressure in a dramatic fashion. If that is not immediately observed by the surgeon, the heart can be ruptured or other significant problems can arise.

One reason that the surgeon attempts to deliver the fluid at a pressure within a certain range is the fact that all of the flow directed towards the heart does not go through the blood vessels for nourishing the heart muscle tissues. For example, the veins which return the blood from the heart capillary beds to the coronary sinus form an intercommunicating network which when cardioplegia solution is delivered in the retrograde direction through the coronary sinus may route a percentage of the solution into veins which actually shunt the blood to the right atrium or into the left ventricle, bypassing the heart tissue. There may also be leakage around a balloon which is used to seal off the blood vessel, typically the coronary sinus, to which the fluid is being delivered. In the antegrade direction, occasionally the aortic valve may be defective or become incompetent due to manipulation of the heart by the surgeon. In either situation, the cardioplegia solution is delivered into the left ventricle rather than the coronary arteries. Therefore, as a result, one cannot be sure that upon delivering a certain amount of fluid, an adequate amount of the fluid will actually go through the tissues of the heart. Surgeons and their perfusionists use the fluid delivery pressure as a measure to indicate adequate delivery to the heart tissues. The particular flow rate necessary to achieve a desired pressure will depend upon the system leakage and the condition of the patient. The placement and seal of the delivery catheter into the aortic root or coronary ostia for antegrade infusion, or into the coronary sinus for retrograde infusion, along with the condition of the patient's blood vessels will also affect whether the flow provided actually moves through the heart tissue. Flow which leaks out of the system will not be useful for maintaining the healthy heart tissue and may contribute to hemodilution and hyperkalemia of the patient.

With most prior blood mixture fluid delivery systems, the control of fluid delivery, as, for example, cardioplegia delivery, is based on the perfusionist's ability to observe changes in pressure and manually adjust the rate of delivery, accordingly. Recently improved devices with an upper pressure unit address only part of the problem. One recently developed device proposes automatically reducing flow rate when an upper pressure limit is reached. Flow rate control returns whenever the pressure is below the set limit. This proposal only addresses part of the inadequacies of prior cardioplegia delivery systems. The true goal should be to provide adequate flow through blood vessels supplying the tissues of the organ or limb. In the case of myocardial surgery, the goal is to have adequate flow to the heart tissues, particularly to the myocardium, at a pressure sufficient to ensure that the principal pathways are adequately perfused but not excessive as to avoid damage to the heart. Excessive pressures may result in rupture of blood vessels, such as the coronary sinus, and should be avoided. However, institution of an upper pressure limit, by itself, would not address the question of adequate delivery through the blood vessels at all times. Thus, safe and adequate delivery of blood mixture fluid to the intended tissue, such as delivery of cardioplegia solution through the heart, is dependent upon the pressure of delivery as well as the flow rate.

SUMMARY OF THE INVENTION

It is an object of the present invention to provide a display panel visually depicting a flow path for a blood mixture fluid delivery system with logical interconnection between two or more visual displays representing two or more controllable characteristics of the blood mixture fluid delivery system. Particularly, it is an object to provide the display panel depicting the flow path of a blood mixture fluid, a display of the blood mixture fluid flow rate and a display of the blood mixture pressure.

It is a further object of the invention to provide a display panel depicting a flow path for a blood mixture which is a cardioplegia solution and depicting a logical interconnection between two or more controllable characteristics of a cardioplegia fluid delivery system selected from visual displays of blood to crystalloid ratio, flow rate, amount of arrest agent, amount of an additive, temperature and delivery pressure of the cardioplegia solution.

It is a further object of the invention to provide a combined flow path display with a separate display panel for selectably displaying information in various modes, programmable target values for various controllable characteristics of the blood mixture fluid delivery system, programming information, system testing information, system warnings and operation instructions. In one particular embodiment, it is an object to provide a combined flow path display and separate selectable information display panel for a cardioplegia fluid delivery system.

It is another object of the invention to provide a display panel with a logical flow path in which one or more of the controllable characteristics of the system may be set using a single adjustable set knob activatable by depressible buttons associated with individual controllable characteristic displays.

It is a further object of the invention to provide visual displays of controllable characteristics of the system will be visually enhanced as with lighting or increased intensity display when that particular controllable characteristic is in a programmable or a set mode.

It is a further object of the invention that priority and emphasis be provided for key or primary controllable characteristics, such as flow rate and pressure, through the use of display positions, display color variations or enlarged visual displays logically interconnected within the schematically depicted system flow path of the panel.

It is another object of the invention that visual displays of controllable characteristics of the system will be displayed with digital readouts corresponding to standard units of measure for the particular controllable characteristic, which is continuously updated according to the actual sensed value or the desired programmed value for a particular controllable characteristic.

Another object of the invention is to provide a display panel for a cardioplegia delivery system in which the direction of cardioplegia flow, whether antegrade or retrograde, is depicted depending upon the selected direction, and preferably to provide a dynamic display by which flow is schematically represented with pulsating or sequentially-activated indicator lights.

It is another object of the invention that an antegrade or retrograde selection valve be provided at the patient or on the instrument with appropriate selectable connections into a limb or an organ, such as the heart or the brain, and that control means be provided on the display panel for selecting pre-programmed antegrade or retrograde controllable characteristics based upon the position of the selection valve. Preferably, a feedback sensory input will be provided from the selector valve to the display panel for automatically determining the valve position so that antegrade or retrograde values and alarms are automatically selected. Further, preferably, a display panel will be provided with positioning controls for the antegrade/retrograde selector valve, which controls are operable from the display panel to simultaneously select and control the position of the valve, sense the actuation to the desired position and invoke parameter values for the controllable characteristics which are desirable for antegrade or for retrograde flow as desired, selected and established.

It is another object of the invention to provide a display panel with both digital upper and lower limits for key controllable characteristics of the system and also, an analog display positioned between the upper and lower limits visually displaying the actual controllable characteristic value of the operating system in relationship to the upper and lower limits. Preferably, an analog display positioned between upper and lower flow limits will be provided. Also preferably, upper and lower pressure limits with an analog display of the actual pressure will be provided on the display panel.

It is a further object of the invention to provide a display panel from which a desired operating control mode may be selected for a cardioplegia delivery system. Preferably, the display panel provides controls for selecting among operating modes, including a set-up mode, a system priming mode, a system running mode, automatic delivery mode based on maintaining a desired pressure, a volume delivered and dose mode, a default parameter setting mode and a timer mode.

It is a further object to provide an information screen adjacent to the flow path representation of the control panel. The information screen is operatively connected to provide useful or helpful information to the user according to the mode of operation, the system parameters, and the condition of the system. Further, preferably function keys and variable function keys are provided on the display panel adjacent to the information screen for receiving operator input responsive to preprogrammed inquiries displayed on the information screen.

It is also an object of the invention to provide controls for operating the blood mixture fluid delivery system at a constant fluid delivery pressure to a patient. Preferably, the constant pressure controls include means for initially adjusting flow rate to obtain a desired delivery pressure and subsequently switching to an automatic constant pressure mode at which the flow rate is automatically adjusted to maintain the desired delivery pressure. Maintaining the delivery pressure constant both avoids excessive pressure which might be dangerous and also facilitates blood mixture flow through all the blood vessels, including small capillaries, for proper delivery to the patient's organ or tissues, such as myocardium, the brain or limbs.

It is a further object of the invention to provide an operator control panel by which an observable volumetric flow rate can be adjustably controlled while observing a resulting patient delivery pressure on the same display panel. Preferably, upper and lower pressure limits are established through said control panel either manually set by the operator or automatically set to preprogrammed limits. Further preferably, it is an object to have an automatic constant pressure mode which can be selectively activated by the operator from the control panel upon obtaining a desired pressure using the adjusted flow rate and the resulting observed patient delivery pressure. Selecting the automatic mode defines a constant pressure which will be automatically maintained through variations of the flow rate. It is a further object of the invention to allow flow rate limits to be either set manually, set according to an algorithm based upon existing pressure limits or set according to an algorithm based upon the actual flow rate at the time the automatic constant pressure mode is selectively activated. When in the constant pressure mode, alarms are provided to inform the perfusionist when the flow rates would be above the high flow rate limit or below the low flow rate limit.

BRIEF DESCRIPTION OF THE DRAWINGS

These and other objects, features and advantages of the invention will become more evident with reference to the drawings in which like reference numerals represent like elements and in which.

DETAILED DESCRIPTION OF THE PREFERRED EMBODIMENTS

Figure 1:
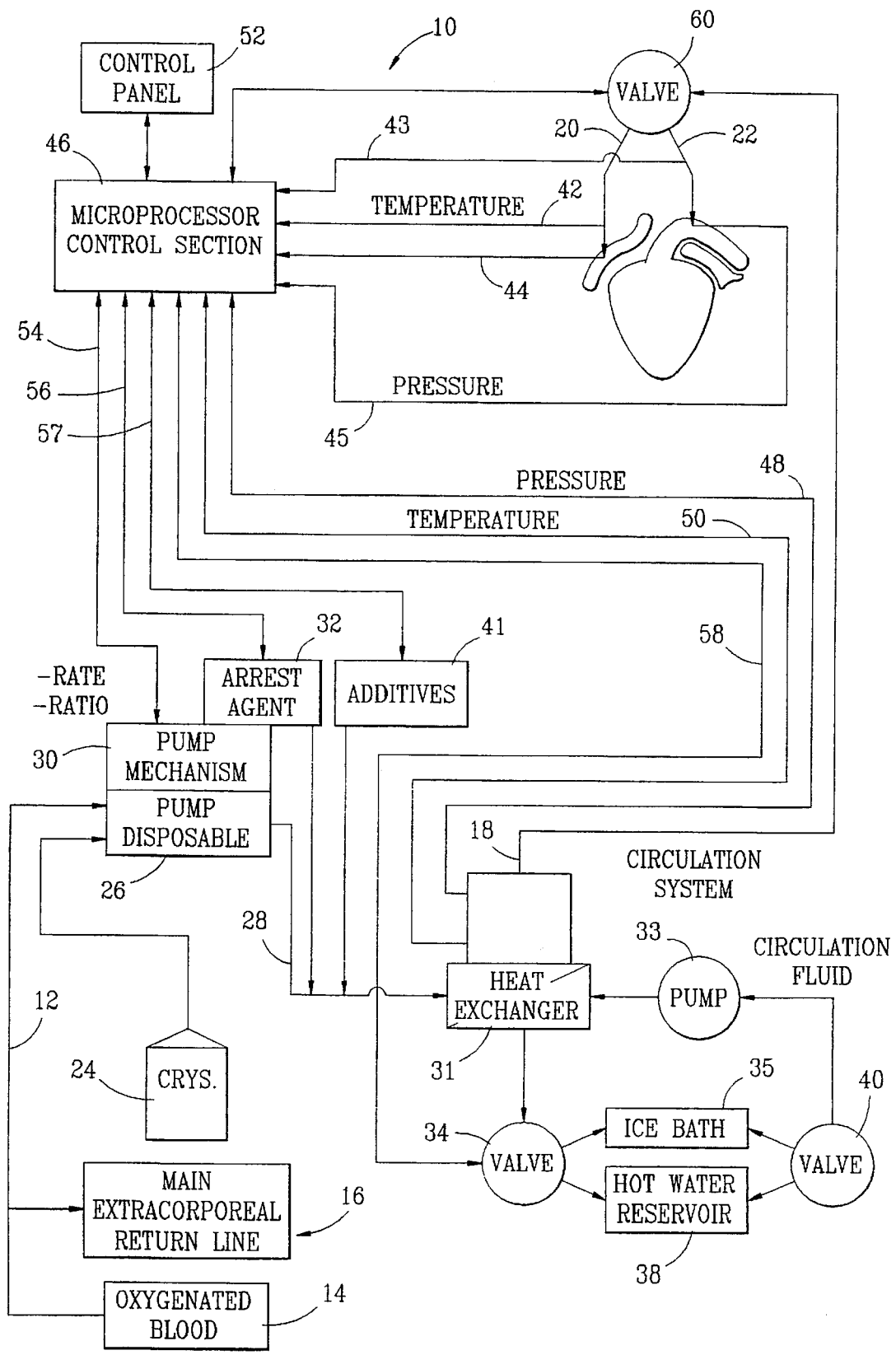
FIG. 1 is a schematic layout of a preferred embodiment of a cardioplegia delivery system for which a display panel according to the invention is useful.

FIG. 1 depicts one embodiment of a blood mixture fluid delivery system 10, which for purposes of example this application will be a cardioplegia delivery system 10. It will be understood that many of the same advantages of the various inventive aspects will also be obtained with blood mixture fluid delivery systems for other medical procedures. For example, isolated limb perfusion, cerebral or neuro-perfusion, or other organ surgery or perfusion for which delivery of a blood mixture fluid will be beneficial. The term "blood mixture fluid", as used herein, shall mean a fluid which consists, in whole or in part, of blood or constituents of blood, such as blood cells, platelets or plasma, which may or may not be mixed with other non-blood constituents according to a particular medical procedure or protocol.

As depicted in FIG. 1, a cardioplegia delivery system 10 is established to provide solution to the heart of a patient during open heart surgery. The principal component of the cardioplegic solution is blood delivered to the system through conduit 12 which is connected to the output of the oxygenator 14 of the heart/lung machine sustaining the patient's vascular system while the heart is isolated therefrom during surgery. Oxygenator 14 provides arterial blood in the main extracorporeal circuit through a return line 16 to the patient's aorta. A fraction, usually about 10%, of the heart/lung machine output is diverted into conduit 12 for processing by the cardioplegic circuit and forwarding to the patient's heart through cardioplegia delivery line 18. The cardioplegic solution flowing through line 18 may be delivered through antegrade line 20 to the aortic root, or through retrograde line 22 to the coronary sinus.

A crystalloid solution is stored in container 24 for combination with blood flowing in line 12 in a disposable pumping cassette 26. The output of cassette 26 is supplied through line 28 to a heat exchanger 31. Pump cassette 26 is controlled by an electromechanical pump mechanism 30 in which cassette 26 is mounted. A second pump 32 containing a heart arresting agent such as a potassium solution supplies its output to line 28 downstream from the pump cassette 26. A third pump 41 may also be included to supply any variety of additives as may be desirable for a particular operation or as may be otherwise requested by the surgeon or by the operating team. The output will be injected into line 28 downstream from cassette 26.

Preferably, pumps 32 and 41 may be syringe pumps or volumetric pouches of a type well known in the infusion art. In the case where pump 32 is a syringe pump, a solution containing a heart arresting agent such as potassium may be loaded into a syringe, and the syringe mounted in pump 32 which progressively depresses the syringe plunger to deliver potassium solution to line 28. The flow rates of potassium solution are less than about 10%, and preferably less than about 5%, of the total flow rate issuing from pump cassette 26. An accurately controllable pump, such as a syringe pump, may be advantageously used in applications where a particular fluid additive or constituent must be an accurately controlled small portion, less than about 10%, of the total flow volume. Similarly, other additives will typically be limited to a small percentage so that accurate control on pump 41 is advantageous.

In the heat exchanger 31, the cardioplegic solution is juxtaposed with a circulating temperature controlled fluid to adjust the temperature of the solution prior to forwarding the solution to the heart through line 18. Preferably pump 33 circulates temperature controlled fluid through the heat exchanger 31 either by push or pull. FIG. 1 depicts a push through coolant system in which a pump 33 circulates the control fluid through heat exchanger 31 and then to a two-way valve 34, which valve 34 may direct the circulating fluid either to an ice bath 36 for cooling or a heated water reservoir 38 for heating. The circulating fluid is then pumped via valve 40 back through the heat exchanger 31 where the cardioplegia solution receives heating or cooling without contamination across a sealed heat transfer material or membrane within the heat exchanger 31.

The system includes patient monitoring of myocardial temperature along the signal path 42 and heart aortic root pressure along signal path 45 or coronary sinus pressure along signal path 44 communicating to a central microprocessor control section 46. In addition, the pressure and temperature of the cardioplegic solution in delivery line 18 is sensed and the data is forwarded along signal paths 48 and 50 to the control microprocessor 46. Data input to microprocessor 46 through control panel 52 may include an advantageous combination of the following parameters:

1. Desired overall volumetric flow rate through disposable pump cassette 26.

2. Desired and measured pressure of the cardioplegia fluid delivered to the patient.

3. Desired blood/crystalloid ratio to be forwarded by disposable pump cassette 26.

4. Desired potassium concentration to be established by pump 32.

5. Desired and measured temperature of solution in cardioplegia delivery line 18.

6. Safety parameters such as the pressure of the cardioplegia solution in the system or upper and lower limits for pressure in the patient.

In response to the data input through the control panel 52 and the monitored conditions along signal paths 42, 43, 44, 45, 48 and 50, microprocessor control section 46 controls the operation of pump mechanism 30 via signal path 54, and of potassium syringe pump 32 by signal along path 56. The control signals for a third pump 41 for additives may be communicated along path 57 between the control section 46 and pump 41. In addition, microprocessor control section 46 controls the circulation of fluid in the heat exchanger circulation path along signal path 58 either for obtaining a desired patient temperature or a desired output solution temperature. Further, the safety parameters such as pressure limits for a particular procedure or a particular patient may be controlled based upon input settings or based upon preset standards, as for example, one range of acceptable pressure limits for antegrade and another range for retrograde cardioplegia. The ranges may be set by the operator or may be set automatically based upon preprogrammed default values or may be calculated based upon preprogrammed algorithms in relation to a selected desired patient delivery pressure.

Communication connections or signal pathways 42, 43, 44, 45, 48, 50, 54, 57, 58 and any others as may be appropriate can be electrical signals through conducting wires, light signals through optical fibers or transmitter radio, ultrasonic or light signals.

In accordance with the invention, the microprocessor controller section 46 controls the pump mechanism 30 to combine crystalloid from container 24 and blood from line 12 in any selected ratio over a broad range of blood/crystalloid ratios. The controller 46 may command the pump mechanism 30 to deliver blood without crystalloid addition. A preferred range for the blood/crystalloid ratio adjustment capability is from 0 to 20:1 or all blood. The rate of flow produced by the pump mechanism 30 of the combined output from disposable pump cassette 26 is preferably variable from 0 to 500 milliliters per minute. The pump mechanism 30 may be operated by microprocessor 46 in either a continuous or intermittent mode by instruction through control panel 52. The arrest agent syringe pump 32 is automatically controlled to deliver at a rate such that the introduction of an arrest agent, such as a potassium solution, to line 28 is automatically maintained at the selected concentration vis-a-vis the flow of disposable cassette 26, without regard to changes requested in the flow rate from pump cassette 26 or changes in the blood/crystalloid ratio, requested of the pump mechanism 30 through microprocessor 46. Flow rates may be requested directly from a control panel by the operator.

Figure 2:
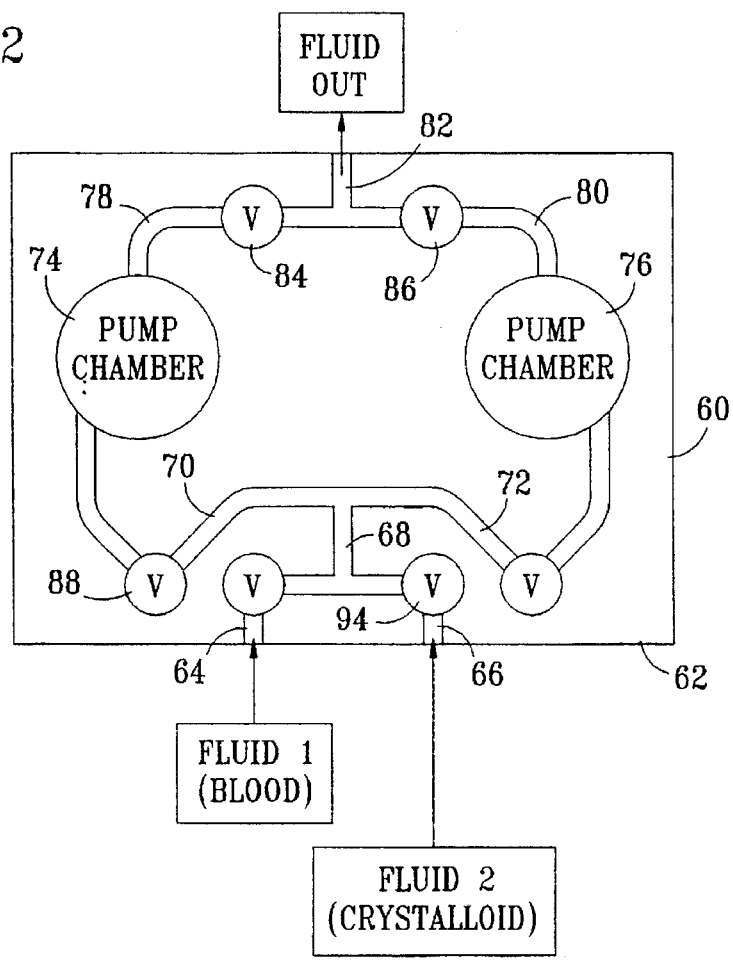
FIG. 2 is a plan view of a disposable pump cassette for a blood/crystalloid combining pump which may be used in the system of FIG. 1.

Disposable pump cassette 26 is illustrated in FIG. 2. The cassette may be formed from two flexible plastic sheets 60 bonded together selectively to form open flow paths and chambers therebetween. Each sheet 60 may be of any simple flexible material such as polyvinylchloride, and the sheets may be radio frequency welded together, leaving the flow paths and pump chambers unbonded. A bladder cassette of this type advantageously reduces the shearing forces and potential damage to which blood might be subjected in other pumps, such as peristaltic pumps.

The entry side 62 of cassette 26 includes a blood inlet 64 and a crystalloid inlet 66. Inlets 64 and 66 lead to a common pump inlet path 68, which is bifurcated to form pump flow paths 70 and 72. Flow path 70 leads to enlarged fluid bladder pump chamber 74 and path 72 leads to an identical fluid bladder pump chamber 76. Outlet path 78 from pump chamber 74 and outlet path 80 from pump chamber 76 are joined at a common outlet 82 from cassette 26 for delivery of the mixed cardioplegic solution to line 28.

FIG. 2 depicts six valve sites located along the fluid paths in cassette 26 according to one embodiment for which the invention is useful. These are sites at which the corresponding flow path may be occluded through operation of a valve plunger on the pump mechanism 30, to press the sheets 60 together at the valve, when the cassette 26 is mounted in operating position in the mechanism 30. Valve 84 is positioned to occlude the outlet path 78 from pump chamber 74. Valve 86 is positioned to occlude outlet path 80 from pump chamber 76. Bladder inlet valves along pump chamber inlet paths 70 and 72 are identified by reference numerals 88 and 90, respectively. Valves 92 and 94 for controlling the passage of blood or crystalloid alternately to common inlet path 68 are positioned at inlets 64 and 66, respectively.

Figure 3:
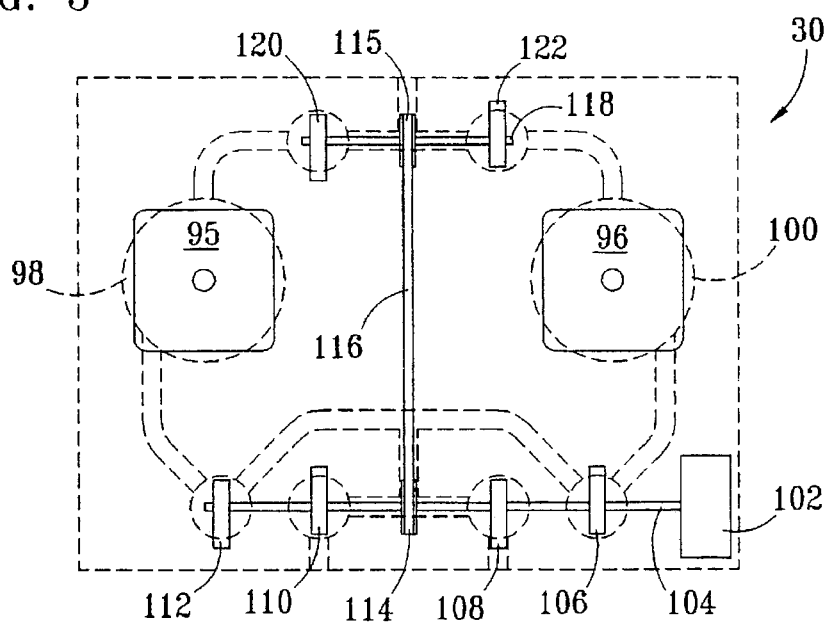
FIG. 3 is a plan view of a pump mechanism for operation of the cassette of FIG. 2.

One embodiment of a pump mechanism 30 is illustrated in FIG. 3, and incorporates a pair of pumping motors 95 and 96. Pumping motor 95 is positioned to advance and retract a bladder driving element 98, and pumping motor 96 is positioned to similarly operate a second bladder driving element 100. Valve cam motor 102 is provided to operate all valve closures on the disposable cassette 26. Cam motor 102 turns an inlet cam shaft 104 carrying valve cams 106, 108, 110 and 112. Cam shaft 104 also turns, by means of pulleys 114 and 115 and timing belt 116, an outlet cam shaft 118. Outlet cam shaft 118 carries valving cams 120 and 122.

Figure 4:
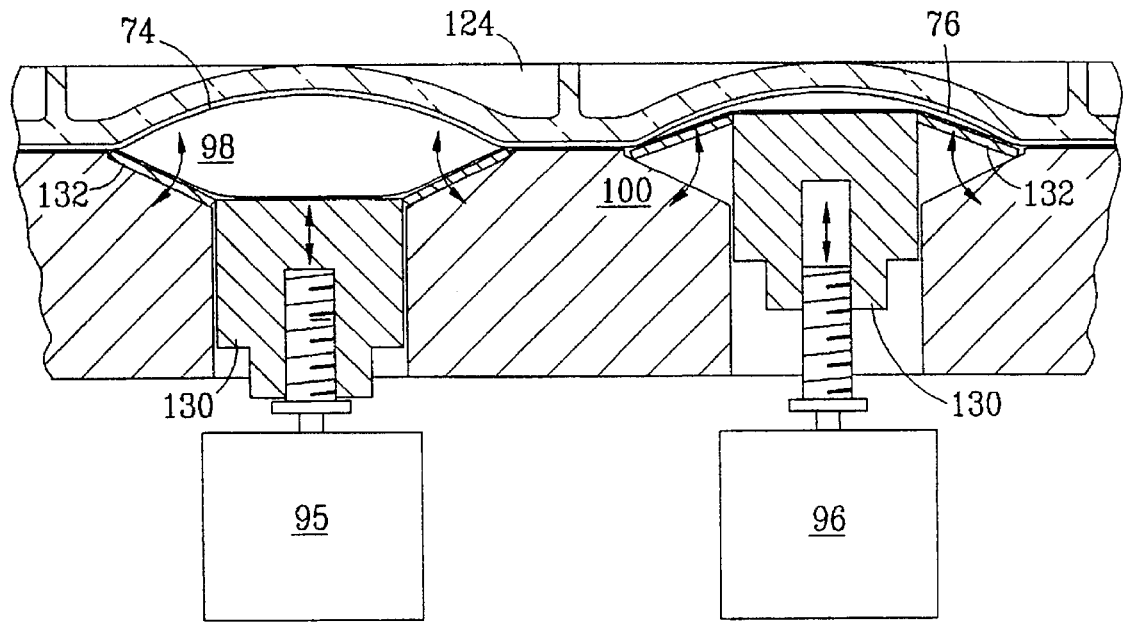
FIG. 4 is a schematic illustration of the functioning of the two pump chambers of FIG. 2.

As best seen in FIG. 4, disposable cassette 26 is positioned tightly against the face of mechanism 30 by a closing door 124 so that the cassette bladder pumping chambers 74 and 76 are enclosed, and confront driving elements 98 and 100. Driving elements 98 and 100 may be of identical construction, and preferably of the petal module type disclosed in U.S. Pat. No. 4,657,490, the disclosure of which is incorporated herein by reference. Although driving elements of this petal module type have the advantage of a linear relationship between displacement by the pump motor and volumetric displacement from the pump chamber, by their close compliance and confrontation to the plastic disposable cassette and by reduced shearing forces associated with the smooth pump action, other driving elements which provide a predictable volumetric displacement by a given advancement of the motor might be utilized.

The variable surface area type of driving element illustrated includes a hub 130, surrounded by radially extending, pivotally mounted petals 132 so that the hub 130 together with the petals 132 provides a confronting surface for the confined pump chamber. Advancement of motor 95 or 96 causes its hub 130 to advance and carry the petals 132 along with it for reducing the volume of the confined pump chamber. Conversely, retraction of motor 95 or 96 causes the corresponding driving element 98 or 100 to retract, withdrawing the constraint on chamber volume.

In FIG. 4, element 98 is illustrated substantially fully retracted, so that pump chamber 74 is filled with fluid, and element 100 is pushed to its full advancement, emptying its pumping chamber 76. Means for measuring the force required to advance each motor, or a pressure sensor contacting the cassette 26 (not shown) is also provided to enable microprocessor 46 to record data representative of the pressure on each bladder chamber.

Figure 5:
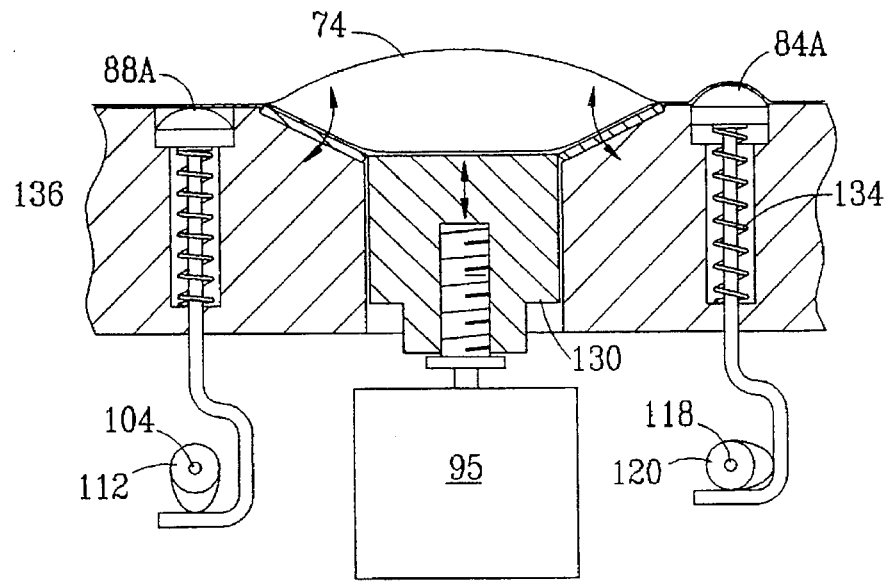
FIG. 5 is a schematic illustration of one pump driver and associated valving mechanisms of the mechanism of FIG. 3.

FIG. 5 illustrates the valving action embodied in mechanism 30, by showing the inlet and the outlet valve arrangement from a single pump chamber. All six valves (90, 94, 92, 88, 84 and 86) and their respective valve cams (106, 108, 110, 112, 120 and 122) operate in similar fashion. Driving element 130 engages the disposable pump chamber 74. Inlet plunger valve 88a and outlet plunger valve 84a, controlled by cams 112 and 120 are normally closed by the action of biasing springs 134 and 136. In the closed condition dictated by the biasing springs, each valve plunger presses against its corresponding valve site on disposable cassette 26 closing the corresponding fluid path. The valve sites 84–94 are each provided with a similar, normally-closed valve. Each of the valve sites 84–94 is opened under the action of valve camming motor 102 upon rotation of its corresponding cam to an open position, retracting the valve plunger from the disposable cassette, and opening the corresponding flow path flow. In FIG. 5, cam 112 has moved to the open position, retracting valve plunger 88A to open valve 88 on cassette 26, opening the inlet 70 of bladder chamber 74 for entrance of fluid.

Figure 6:
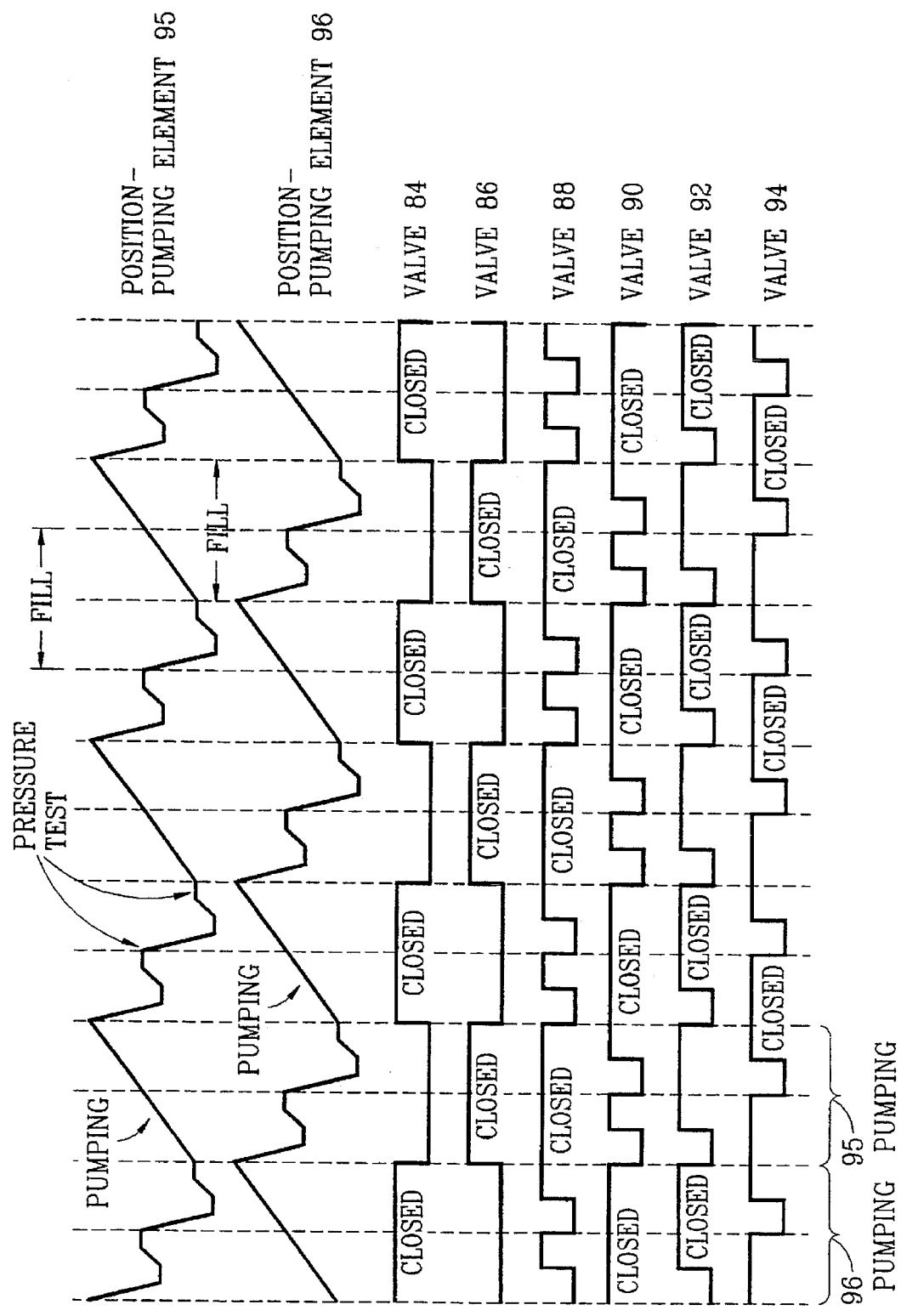
FIG. 6 is a timing diagram illustrating the cycle of the blood/crystalloid pump depicted in FIGS. 2–5.

FIG. 6 illustrates a timing diagram for the operation of the valve cam motor 102 in conjunction with the pumping motors 95 and 96. In the cycle described, one chamber pumps a mixture of blood and crystalloid in a selected ratio outwardly from outlet 82 of cassette 26, while the other pumping chamber is undergoing a sequential fill and test protocol. Filling chamber is filled with blood to the volume to produce the desired ratio followed by pressure testing of the chamber with its inlet and outlet valves closed to verified capture of the desired amount of blood. Following this step, the drive element of the filling pumping chamber is further retracted and another constituent of the blood mixture fluid, in this embodiment crystalloid solution, is admitted to complete the filling of the chamber. Then the inlet and outlet valves on the filling chamber are closed to pressure test the chamber for a captured full load. Additional pressure tests and monitoring may be conducted in one chamber during pumping by the other chamber to determine if there is any unsafe occlusion or to control the pressure within an appropriate safe range for a given procedure. The unique two-chamber construction advantageously allows such testing without any interruption to the constant flow of fluid.

Thus, at the commencement of the FIG. 6 diagram, the pumping chamber bladder 74 has been emptied, and the other bladder 76 is full of a blood-crystalloid mixture in the desired proportions. The outlet valve 84, from chamber 74 is closed. Outlet valve 86 is open to pass the combined fluid from chamber 76 through the outlet 82 to the heat exchanger 31 at the requested volumetric flow rate. Throughout the period of delivery from chamber 76, its inlet valve 90 remains closed, and the corresponding pumping element 100 is advanced by motor 96 to reduce the volume of bladder 76 to expel the blood/crystalloid solution. The speed of motor 90 is governed by the requested flow rate. A volume rate control knob 166 on display control panel 52 is used by the operator to adjust the requested flow rate and through processor 46 the speed of motor 90 is correspondingly adjusted. The outlet valve 84 from chamber 74 remains closed throughout this period of pumping from chamber 76.

The valves 92 and 94 controlling inlet of blood and crystalloid to common inlet path 68, and the inlet valve for chamber 74 are sequentially opened and closed during the filling protocol for bladder 74, which occupies the time period during which bladder 76 is delivering fluid to line 28. Thus, when one bladder has completed its pumping step, the other has received solution constituents in the desired ratio and is ready to deliver. Substantially continuous flow is thus enabled. In the 4-step filling protocol for chamber 74, illustrated at the outset of the diagram, valves 92 and 88 are initially open, and valve 94 closed. Thus, an open flow path for entry of blood to chamber 74 is provided through inlet 64, common path 68 and pump chamber inlet path 70, while crystalloid is occluded at valve 94. Pump motor 95 is retracted sufficiently to admit sufficient blood to comprise the desired fraction of total chamber volume. Then valves 92 and 88 are closed, and pump motor 95 is advanced a few steps, to confirm by elevating pressure that the requested blood load has been captured between closed valves 88 and 94. With confirmed introduction of the correct amount of blood, valves 88 and 94 are opened while valve 92 remains closed to stop further blood entry. The pump motor 95 now retracts to admit the correct volume of crystalloid along paths 66, 68 and 70. This is followed by closing valves 88 and 94. Motor 95 is advanced briefly to confirm by pressure elevation that the full incremental volume has been occupied by crystalloid solution. With this confirmation, the fill protocol is complete, and chamber 74 is ready for delivery on the completion of delivery from chamber 76. As chamber 74 then delivers, chamber 76 undergoes a similar 4-step filling protocol.

It will be appreciated that a change in the ratio of blood to another constituent, such as crystalloid, is a simple adaptation for the pump mechanism 30. In the diagram, the retraction of the pumping element during blood fill and crystalloid fill is depicted as substantially equal. If a different ratio is requested through control panel 52, microprocessor 46 simply directs the motors 95 and 96 to retract by different amounts during their blood-fill and crystalloid-fill steps. The full retraction of a motor is the same for the combined fill. It is simply necessary to adjust the amount of retraction during each fill step to the requested ratio. The ratio may be continuously adjusted from 100% of blood to 100% crystalloid. Thus, if the requested blood/crystalloid ratio is R, and the motor driven-volume displacement relationship is linear:

$$R = \frac{\text{Number of motor steps retracted during blood fill}}{\text{Number of motor steps retracted during crystalloid fill}}$$

The total volumetric flow rate from the cassette is varied pursuant to operator request simply by compressing or expanding the time for a cycle to be completed. Of course, if intermittent operation is desired, this may be provided as well.

No matter what changes may be made to the blood/crystalloid flow rate, microprocessor 46 preferably automatically controls the arrest agent pump 32 to deliver at a rate which provides the requested percentage of the then-existing blood/crystalloid flow rate.

One or more other additives may be added to the blood mixture fluid as with an additive pump 41 which is controlled from control panel 52 through microprocessor 46 and along signal path 57. Typically, any combination of additives may be premixed for insertion through one additional pumping mechanism 41, although another could also be incorporated in a similar manner, separately controlling the amount of individual constituents or additives. As with pump 32, the ratio can be automatically maintained according to the flow rate of pump 30. This advantageously facilitates the capability of this mechanism to function in an automatic constant pressure mode, where the flow rate may be continuously varied to maintain a constant pressure according to the present invention.

The improved and simplified control over blood mixture fluid delivery, which is enabled by this invention, and the improved solution handling are believed to represent a significant tool specifically for the heart surgeon/perfusionist team, as well as for other health care teams which may require controlled pumping or recirculation of blood mixed with one or more other fluids.

Figure 7:
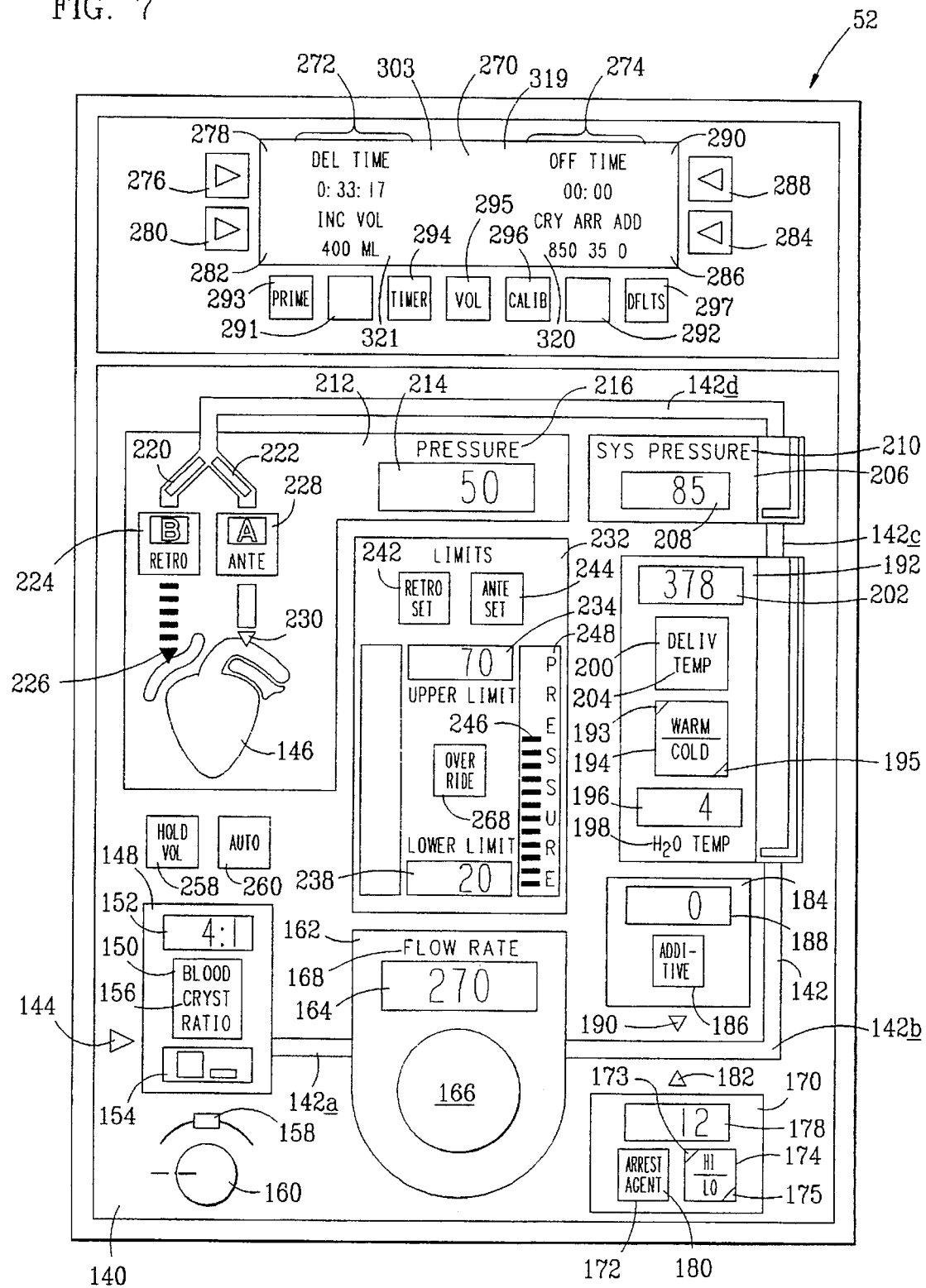
FIG. 7 is a front plan view of a preferred embodiment of a display panel according to the present invention.

FIG. 7 is a detailed perspective view of a preferred embodiment of display panel 52. Display panel 52 has a front face 140 which is viewable from a wide frontal angular area, including substantially 180°. In the preferred embodiment, a substantially flat face 140 works well and is constructable using standard molding techniques, stamping techniques and components. Advantageously, a flow path 142 is visually depicted on the front panel interconnecting with portions of the substantially visually continuous flow path interconnecting two or more system component display areas, as with interconnecting portions 142a, 142b, 142c and 142d. Preferably, the two or more system components are those which are those system components which represent characteristic elements of the system which are adjustable through controls operably interconnected with the control panel 52, such as through a microprocessor control section 46 (as shown schematically in FIG. 1.) Also preferably, the visual depiction of the flow path 142 is formed with sufficient width and having sufficient contrasting color between the flow path 142 and the face 140, as for example, with a red flow path line 142 on a white or light beige or light grey background base 140. A width of approximately 3/16 of an inch to 5/16 of an inch (about 0.5 cm to 0.8 cm) with a bright oxygenated blood red color on a light grey background has been found to be easily visually perceptible from normal viewing distances in an operating room. It being observed that the normal maximum distance which the perfusionist is likely to move from a control panel during an operation will be about 9 to 15 feet (about 3–5 meters).

Prior control mechanisms for cardioplegia fluid delivery typically have various separate and independently located controls and visually independent displays separately connected with the various independent controls. Thus, the present control panel 52 advantageously incorporates at least two system component displays on the same display panels, which system components are located along a visually perceptible flow path 142, preferably in a logical sequence, which is characteristic of a cardioplegia perfusion system.

While the invention will be described in connection with a preferred embodiment in which display areas for all the major controllable characteristics or parameters of a cardioplegia system, all located in a logical sequence, it will be understood by those skilled in the art that many of the advantages of the inventive display can be obtained through placing displays of at least two or more controllable parameters of a blood mixture fluid delivery system on a single display panel arranged and interconnected in a logical sequence along a flow path. By way of example, and also because of the many specific advantages of the invention for open heart surgery, the invention will be described below in connection with a cardioplegia delivery system 10.

In the preferred embodiment, the flow path is provided with a start indicator, such as an arrow or arrowhead 144, which may be illuminated when the system is in an "on" position. Also, the flow path 142 is provided with a depiction of the delivery and of the flow path, as with a depiction of an organ, limb or other part of a patent, such as a heart 146, at the opposite end of the flow path from the start 144.

One of the first components which has desirably adjustable characteristics for the perfusionist is a blood-to-crystalloid ratio display area 148 and the display area 148 includes an adjustment actuation button 150, a digital display 152, a dynamic pump action display 154, and a label 156 associated with the digital display 152 and the dynamic pump action display 154 so that the operator will immediately understand which component of the system is represented by those displays within area 148. Whenever the pump is operating, display 154 is animated to show up and down pump action so that the operator immediately recognizes whether the system is operating. Upon depressing adjustment button 156, the set mode is actuated for establishing a desired blood-to-crystalloid ratio. Preferably, button 150 becomes lighted to indicate it is in an adjustment mode or a "set-up" mode and the digits within digital display 152 become brighter so that the operator is immediately notified that the blood-to-crystalloid ratio is in a condition for being set. Also, a set indicator light 158 display is comes on or is otherwise lighted and the adjustment knob 160 is activated for manually adjusting the desired blood-to-crystalloid ratio, which adjustments will be continuously displayed within digital display 152. Once the desired ratio is established, then the operator again toggles the button 150 so that it is in an out position, turning off the light therebehind, dimming the digital display 152 and disconnecting knob 160 so that the set light 158 goes off.

The operation of the adjustment knob 160 in connection with setting various ones of the adjustable parameters of the system will be explained more fully below with respect to FIGS. 4–7. For a preliminary understanding of the preferred embodiment, the set knob 160 is engageable with the adjustment actuation switches or buttons which are associated with various ones of the display areas for components of the system which may be periodically adjusted. These components do not necessarily require adjustment for each patient so that a single adjustment knob 160 can be used with separate components while the others are maintained at a previous setting.

Flow rate display area 162 includes a digital display area 164 and a continuously engaged flow rate adjustment knob 166. The flow rate display area 162 also includes a label 168 adjacent to the digital display 164 so that the operator, perfusionist or surgeon immediately associates the digital display with the appropriate adjustable characteristic or parameter of the system. As the flow rate is typically the primary variable feature with respect to each patient, the adjustment knob 166 is continuously engaged and does not require actuation of an adjustment switch in order to engage the adjustment knob. The perfusionist may variably dial in the flow rate as required for each patient. It will be seen in the embodiment depicted in FIG. 7, flow rate area 162 follows closely adjacent to the blood-to-crystalloid ratio display area 148 along flow path 142 as it is a logical sequence corresponding to the system depicted in FIG. 1, in which the blood and crystalloid is pumped to the patient. The flow rate controls the rate of pumping. Its position on the display through a visual and logical correlation to the system which is understandable by the perfusionist and which reduces confusion and facilitates quick reaction by the perfusionist to any changing conditions during surgery. Normally, the perfusionist gradually increases the flow rate from a low initial value up to a desired pressure value, while watching an indicator of the pressure of the cardioplegia fluid at a catheter interconnected with the heart. The desired pressure will depend upon overall considerations, including whether the system is being operated in a retrograde flow or an antegrade flow direction. The perfusionist typically approaches the desired pressure slowly so that damage to the blood vessels supplying the heart with cardioplegia fluid is avoided. A constant pressure can be defined by selecting an automatic constant pressure mode of operation when the desired pressure is reached by manually adjusting the flow rate.

As used in this application, the term "defined", when used to describe a particular value or a particular controllable characteristic, such as a "defined flow rate," a "defined pressure," a "defined concentration," a "defined temperature" or other defined characteristic or value, will have a meaning which includes any established value or characteristic, including a value or a characteristic as desired by perfusionists or surgeons, or a value or characteristic which is set by the perfusionist or doctor at the time of surgery, a value or characteristic which is predetermined by the perfusionist or doctor, a value or characteristic which is predetermined by established protocol for a particular procedure, a preset value, a value which is calculated by the microprocessor control according to preprogrammed algorithms, or a value which may be existing in the microprocessor memory, such as a default value or such as the last value set during a previous procedure using the same machine.

In normal cardioplegia delivery, as depicted in the system indicated in FIG. 1, an arrest agent will be added to the cardioplegia fluid at one high level of concentration initially in order to stop the heart from beating and subsequently after the heart has been sufficiently stopped from beating, will be maintained in an arrested condition with a low concentration of the arresting agent in the cardioplegia solution. Correspondingly, on the control panel 52 of FIG. 7, the arrest agent display area 170 preferably includes an arrest agent adjustment switch 172 which may be a depressible two position switch and also a high or low concentration selection switch 174, both of which are activatable to engage adjustment or set knob 160 and cause the set light 158 to light up. The digits in digital display 178 will also become brightened when the adjustment switch 172 is activated. When the value of the arrest agent concentration displayed in digital display 178 is greater than zero, then an on indicator light 182 will become activated. Preferably, the on light is in the shape of an arrow or arrowhead, which visually conveys the concept that an arrest agent will be entering the flow path 142 which will be carried to the heart 146 of the patient. Uniquely, the high concentration or high amount of arrest agent (i.e., the amount or mixture which will stop an initially beating heart) can be adjusted separately from the adjustment of a low concentration merely by pressing or toggling the high or low selection switch 174. The different concentrations can also be selected for delivery to the patient by merely pressing or toggling the high or low selection switch 174. After the heart is stopped with a high concentration, a lower concentration of arrest agent will maintain the still heart. The perfusionist can adjust the low level of arrest agent separately and then during operation can select a low arrest agent supply to the patient. Switching from high to low and back again is advantageously a one-button procedure.

At any time before or after the blood-to-crystalloid ratio is established and a flow rate begins with or without an arrest agent, a surgeon may determine that an additional additive should also be included within the cardioplegia solution. For this purpose, the additive may include one or more medicinal solutions or compositions and the option for controlling the addition of this additional additive is provided with a display area 184, including an adjustment activation switch 186, a digital display 188 and an on or additive included light 190. When the value in display 188 is zero, the light 190 is off and when it is greater than zero, then light 190 comes on to indicate to the perfusionist and those observing the control panel display that an additive is being included.

Once the solution is complete as to its composition, then it will be heated or cooled depending on the requirements of the particular phase of the heart operation. Typically, during a myocardia procedure, the heart will be cooled with a cold bath during the operation and will be warmed subsequent to the operation in order to revive operation of the heart. Depending on the protocol of the operation involved, various phases of heating and cooling of the heart may be required. The heat exchange or display area 192 includes a switch 194 by which the temperature of the warm bath or the temperature of the cold bath may be alternatively detected and viewed at display 196, which is associated with an understandable label 198. A delivery temperature adjustment switch 200 is provided which upon depressing engages the set knob 160 and lights up the set light 158 to adjust the desired delivery temperature which is display in a digital display 202. A label 204 is provided adjacent the digital display 202 and preferably, is on or associated with the adjustment switch 200 which indicates that this digital display is representative of the delivery temperature. Again, when the delivery temperature adjustment switch 200 is activated, it will become lit and digital display 202 will increase the light intensity so that the perfusionist will immediately understand that adjustment using knob 160 is directed to the delivery temperature.

Another characteristic of the system which advantageously provides information to the perfusionist is the system pressure such that a system pressure display area 206 is provided with a digital display 208 and a label 210. Normally, the system pressure depends upon the flow rate and the patient delivery pressure, and also upon the particular configuration of the system. An inordinately high system pressure can indicate a kink, bend, or blockage in a tube or other potential problems. For example, where the system pressure is substantially higher than the patient delivery pressure, then in that event, there may be a risk that through movement of the delivery tubing or the delivery catheter, an obstruction may be alleviated which will result in an excessive system pressure temporarily becoming a potentially dangerous excessive patient delivery pressure. The perfusionist can be on guard for such a situation and can thus be ready to respond for the safety of the patient.

A preferably adjustable key characteristic or parameter of the system is the patient delivery pressure. This may be measured at a catheter or cannula at which the system is connected to the patient's blood vessels. A readout of the patient delivery pressure is included within a delivery pressure display area 212. A digital display 214 with an appropriate label 216 is provided. Preferably, both the flow rate display 164 and the delivery pressure display 214 are positioned centrally located for ease of observation and the attention of the perfusionist as they are substantially key characteristics of the system. Also preferably, the flow rate display 164 and the pressure display 214 are larger than the other subcharacteristic displays so that attention is immediately drawn to these features without undue "hunting" by the operator. It will be understood that for any given patient and system set-up the flow rate and delivery pressure of the system are inter-related. Thus, for a given set-up, tubing size and integrity of the connection or catheterization to the patient, increasing the flow rate will normally increase the pressure. If there are restrictions in the flow path, it will be more difficult to move the same amount of cardioplegia fluid through the same tubes and blood vessels. This will tend to cause both a lower flow rate and a higher pressure.

Controls for such a system will operate according to these principles, for example, if a lower pressure is required, a lower flow rate must be set. If a higher pressure is required, a higher flow rate must be requested. However, if a change in the system occurs, such as a restriction at the delivery catheter, the pressure will tend to increase and the flow will tend to decrease. If a constant flow has been requested, the pressure must go higher to maintain the same flow rate throughout the restriction. If a constant pressure has been requested, the flow rate must be decreased to maintain the same pressure at the restriction.

Figure 8:
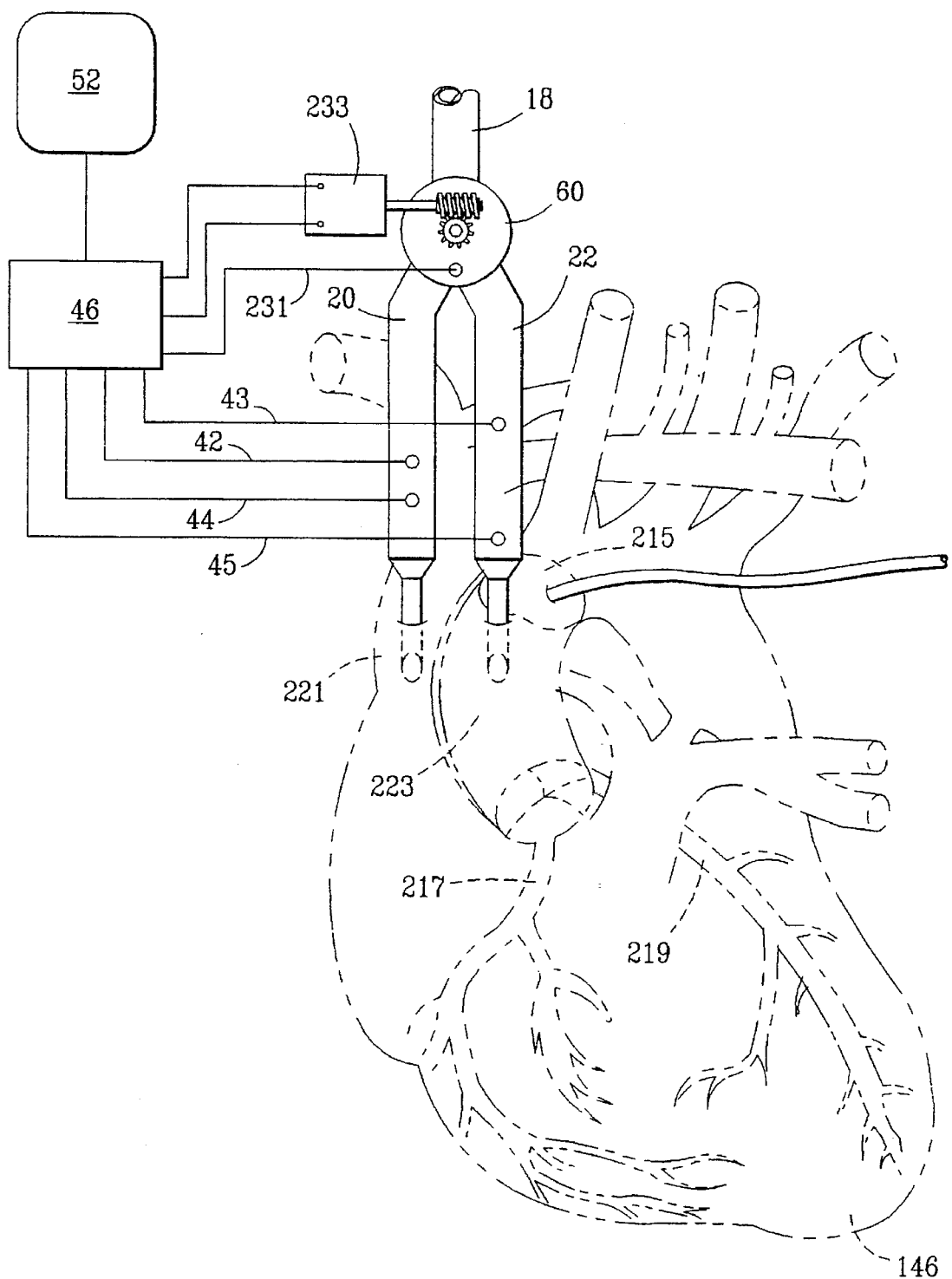
FIG. 8 is a schematic plan view of a simplified cardioplegia system connected for selectable antegrade or retrograde fluid flow.

Also important in the delivery of blood mixture fluid, and particularly cardioplegia fluid to a patient, is the direction of blood flow through the blood vessels. A schematic depiction of a directional valve connected to antegrade and to retrograde catheters to a heart is depicted in FIG. 8. Antegrade flow through the blood vessels of the heart is the normal blood flow direction with the cardioplegia solution entry through the aortic root 215 or the coronary ostia, flowing in through the coronary arteries 217 and 219, through the muscles, and out through the veins. Alternatively, the cardioplegia solution may be delivered in a retrograde fashion through a catheter 20 engaged in the coronary sinus 221 so that the cardioplegia solution is pumped into the veins, back through the muscle tissue and out from the arteries. Typically, the retrograde flow of cardioplegia fluid is desirable when there is substantial coronary blockage so that the tissues adversely affected by the arterial blockage will receive or have a chance of receiving cardioplegia solution while the blockage is bypassed during the surgery. In any event, the acceptable pressure for the system in the antegrade direction is different than the acceptable pressure in the retrograde direction. In the antegrade or normal direction of blood flow, the coronary arteries are thick walled vessels accustomed to normal systemic blood pressure ranges, typically exceeding 100 mm Hg; therefore, to achieve normal distribution, high perfusion pressures are necessary. Delivery at a constant defined pressure ensures that the volume of flow actually reaches the tissues so that they are adequately perfused. Merely limiting the uppermost pressure avoids blood vessel damage but would not address the need for adequate delivery. Conversely, in the retrograde direction, the cardioplegia solution is delivered via the coronary sinus into the coronary veins. The coronary sinus and coronary veins are thin walled vessels accustomed to low pressures, typically less than 20 mm Hg; therefore, it is dangerous to expose these vessels to the higher pressures required for antegrade delivery. Yet, adequate flow to the tissues is optimized when the pressure can be held constant at a desired level. The constant pressure also automatically avoids unsafe high pressure.

Surgeons change the direction of delivery to achieve optimum distribution of cardioplegia solution. The pressure must also be adjusted accordingly. Because of the different delivery scenarios, it is advantageous to have a system control panel which is intuitive by logical depiction of the system flow paths. Establishing a defined pressure and flow rate for the particular setup, whether antegrade or retrograde, is facilitated by clear visual depiction of the flow direction. Once the appropriate flow and pressure are established, as through slowly increasing the flow until the appropriate pressure is reached, then the system can be switched to a constant pressure mode to continue optimum delivery to the patient.

A visual display is provided in which indicators 220 and 222, such as an indicator light 220 indicating retrograde flow and an indicator light 222 indicating antegrade flow will be activatable by the perfusionist depending upon the system connections and catheterization of the patient. There is also a retrograde adjustment switch 224 and a retrograde flow "on" light 226, as well as an antegrade adjustment switch 228 and antegrade flow "on" indicator 230. In a preferred embodiment, flow lights 226 and 230 are dynamic or animated indicators which have flashing or a sequentially illuminated series of lights which give the appearance of movement toward the heart along the flow path corresponding to the operating mode of the system at the time. If the flow stops, the dynamic lighting or animation of flow also stops; this condition is immediately perceivable by the perfusionist or the surgeon.

The function of the retrograde switch 224 and the antegrade switch 228 will be discussed more fully below with various preferred embodiments. Initially, in a basic mode the switches 224 and 228 are provided so that the perfusionist can select from the panel which flow direction is to be displayed. The selection of the flow direction may depend upon the indication from the surgeon which direction is activated by the surgeon. Activation of the switch by the perfusionist will activate different sets of default limits and alarms and as the delivery pressure displayed at 214 is typically a reading which is detected at the entry catheter, whether in the aortic root or in the coronary sinus, so that appropriate input to the display 214 is determined by selection switches 224 or 228.

In further preferred embodiments, the patient is connected for either retrograde or antegrade flow with a cardioplegia diversion valve 60 interposed so that the surgeon may select between antegrade or retrograde flow during surgery. The antegrade switch 228 and the retrograde switch 224 may in the preferred embodiment be connected at sensor 231 to detect the position of the valve 60 automatically and toggle between the appropriate positions. Alternatively, actuation of switches 224 or 228 by the perfusionist may actually be connected to control section 46 for actuation of a servo motor 233 for controlling the position of the valve 60 so that it can be caused to move from the control panel 52, between retrograde and antegrade flow directions as desired. As with each communication connection between the display panel 52 and control mechanisms for the system 10, the signals may be electrical signals carried by wire, radio signals transmitted between the panel, the control circuitry 46 and/or the various control mechanisms.

During surgery, it is advantageous to continuously monitor the operation of the system. It is also advantageous to allow the perfusionist a certain degree of freedom to attend to various matters, such that alarm limits may be set. A limit display section 232 is advantageously provided in which an upper limit display 234 and a lower limit display 238 are provided. Initially, the upper and lower limits are set by default or by the perfusionist to establish maximum and minimum safe patient delivery pressure. The actual pressure corresponding to the patient delivery pressure at display 214 and the actual flow rate to the patient is advantageously depicted with an analog pressure display 246, which is positioned between the upper and lower limit digital displays 234 and 238. The perfusionist can visually observe the relationship of the patient delivery pressure as digitally displayed at display 214 in relationship to the upper and lower limits 234 and 238. A lighted label 248 is provided in the analog display area 246 to clearly indicate which limits are being observed.

Figure 9:
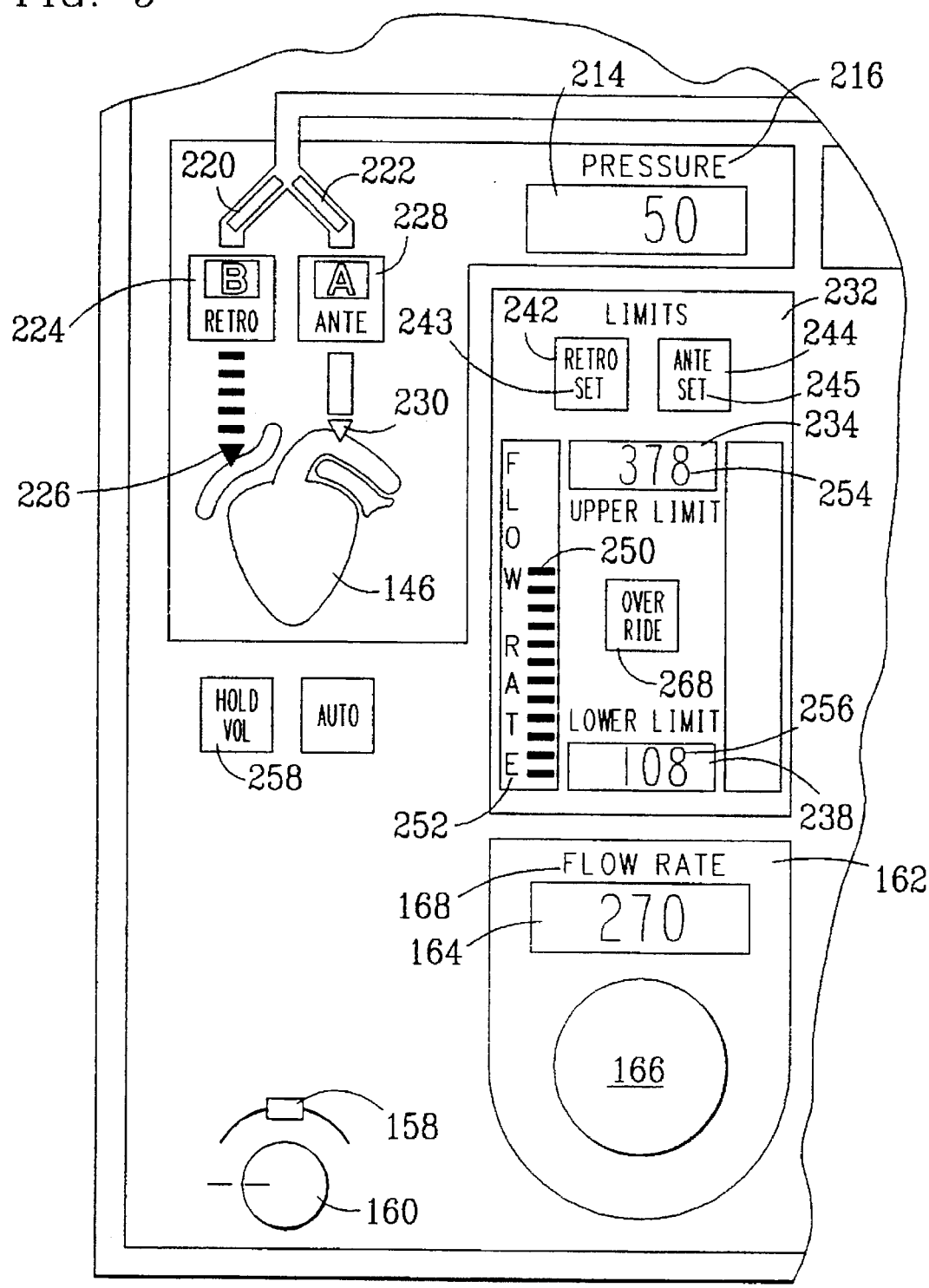
FIG. 9 is an embodiment of a display panel with flow rate controls and digital displays of flow rate, pressure and upper and lower limits and with analog displays for operating parameters relative to the digitally displayed limits.

The safe limits will be different for antegrade flow or for retrograde flow directions. Setting limits separately, depending upon flow direction, may be accomplished with retrograde adjustment switch 242 and with antegrade adjustment switch 244. Depression of either switch 242 or 244 will activate the set knob 160 so that the upper and lower limits can be adjusted for each flow direction. It is noted that the operator may view the limits separately for the antegrade and the retrograde flow direction. As shown more clearly with reference to FIG. 9, the same display area upper limit 234 and lower limit 238 can be used in connection with a flow rate limit display in which an analog display 250 of the actual flow rate is provided and has a lighted label 252 to clearly indicate that the upper flow rate limit 254 is activated and the lower flow rate limit 256 is activated. Again, the upper and lower flow rate limits can be separately set by the operator or by the control section 46 for retrograde and for antegrade flow through the patient's heart. The antegrade switch 244 and retrograde switch 242 may be used to separately display and/or set the limits. In the normal operation of cardioplegia delivery, the perfusionist has control over and adjusts the flow rate with knob 166. This condition is preferably the default condition during the normal run mode.

It has been found advantageous, during surgery and during continuous operation of a cardioplegia delivery system in the run mode, to maintain a defined constant pressure. As used here, delivery at a constant pressure means more than simply avoiding an upper limit. Adequate flow also requires keeping the pressure above a certain lower limit. Delivery at a constant pressure addresses both avoiding potentially unsafe high pressure and also inadequate low pressure. Delivery to the target tissue is optimized at a defined constant pressure within the range of a safe upper limit and adequate delivery lower limit. As pressure for a given cardioplegia system is dependent upon and proportional to the flow rate, automatic microprocessor control of the flow rate can be programmed in order to maintain a defined pressure. Some of the advantages of a constant pressure delivery system include the prevention of excessive pressures which can cause physical damage to the heart while keeping the capillaries expanded or dilated for optimum delivery. The use of upper and lower flow rate limits ensures adequate delivery to the heart tissues when a constant pressure is maintained. For example, it is not unusual for the retrograde cannula to become dislodged from the coronary sinus, resulting in delivery of the cardioplegia solution to the right atrium rather than to the heart tissues.

In some prior existing systems, the surgeon must rely on periodic visual monitoring of pressure to ensure that the catheter is in place. With the use of constant pressure delivery with upper and lower flow rate limits, the instrument microprocessor will immediately detect any change in pressure caused by the dislodged cannula and will compensate by increasing flow rate. When it is "evident" to the microprocessor, as through preprogrammed limits or algorithms, that the defined constant pressure cannot be maintained while remaining within the limits of flow rate, the instrument will sound an alarm, alerting the perfusionist and surgeon to the problem. In other situations, when some leakage exists in the connection between the cannula and the blood vessels, increasing the rate of flow may maintain the defined constant pressure so that adequate flow to the tissues is maintained despite the leakage.

In a method of operation of the instrument, at the beginning of a perfusion procedure, the perfusionist will ramp up flow rate by manually adjusting flow rate knob 166 until a desired or predetermined pressure is achieved. After the flow rate is established at a more or less steady state at which a desired or a predetermined pressure is being maintained, then the perfusionist may, in a preferred embodiment, activate an automatic pressure maintenance mode with switch 260. This defines the constant pressure. The flow rate would then be automatically varied, as by control signals from the microprocessor, to keep the existing defined pressure. The upper and lower pressure limits would no longer be appropriate or necessary. The appropriate limits would be those for the flow rate. Upper and lower flow rate limits may be set by the perfusionist or preferably, according to one embodiment of the present invention, may be automatically established based upon a reverse proportionality ratio calculated from the previously existing upper and lower pressure limits and the existing flow rate and defined pressure at the time the automatic constant pressure mode is activated.

In a preferred embodiment, the operation of the pump is controlled to allow automatic pressure maintenance. Operating limits for pressure are selected for both high and low pressure limits. The selection may be made by the operator or may be automatically set by the control system. Normally, the flow rate of the pump is increased gradually by the operator and the resultant pressure is observed. A desired or predetermined operating pressure, for example, 50 mm Hg for retrograde flow, may be established. At this point, if the flow rate meets the criteria that the user expects for an operating pressure of 50 mm Hg, an "automatic" button 260 or a constant pressure button 260 may be pushed. Activation of the "automatic" button is preferably optional so that the delivery system can be used by a perfusionist or a surgeon who is uncomfortable with, or simply not accustomed to, the advantages of a constant pressure blood mixture delivery system.

Once the automatic button 260 is pushed, the pressure which is displayed at 214 becomes the desired operating delivery pressure and the flow rate begins to vary automatically according to program controls to maintain that pressure. In addition, the alarm limits for the operating system become high and low flow rate limits. Advantageously, these flow rate limits or alarm rates may be calculated and set by using the operating delivery pressure, the flow rate, and the pressure alarm limits that are in effect when the "automatic" button is pushed, i.e., when the change is made to constant pressure operating mode. Calculation of the new limits will be based upon a preprogrammed algorithm of proportionality. For example, if at a particular flow rate of 300 ml/minute, there is an operating pressure of 50 mm Hg and if pressure alarm limits have been set at 20 mm Hg lower limit and 70 mm Hg upper limit, the new proportional flow rate limits might be calculated as follows:

$$\frac{\text{Lower Flow Rate Limit}}{\text{Lower Pressure Limit}} = \frac{\text{Flow Rate}}{\text{Pressure}}$$

$$\text{Lower Flow Rate Limit} = \frac{\text{Flow Rate}}{\text{Pressure}} \times \text{Lower Pressure Limit}$$

$$= \frac{300 \text{ ml/min}}{50 \text{ mm Hg}} \times 20 \text{ mm Hg}$$

$$\text{Lower Flow Rate Limit} = 120 \text{ ml/min}$$

$$\frac{\text{Upper Flow Rate Limit}}{\text{Upper Pressure Limit}} = \frac{\text{Flow Rate}}{\text{Pressure}}$$

$$\text{Upper Flow Rate Limit} = \frac{\text{Flow Rate}}{\text{Pressure}} \times \text{Upper Pressure Limit}$$

$$= \frac{300 \text{ ml/min}}{50 \text{ mm Hg}} \times 70 \text{ mm Hg}$$

$$\text{Upper Flow Rate Limit} = 420 \text{ ml/min}$$

As long as the pump operates between those flow rate limits, no alarm limit is exceeded. In the event that the rate required to maintain the pressure exceeds the operating upper limit, there are certain visual operating conditions which make the user aware that the upper limit has been reached.

The upper and lower limits are established to activate various alarm systems which in the preferred embodiment will include a period of flashing displays, such as a flashing upper limit when the upper limit is approached or a flashing lower limit when the lower limit is approached. This might be used in conjunction with an audible alarm. Alternatively, an audible alarm may be initiated after a given time period of warning flashing. Subsequent to a warning alarm in combination with the flashing lights, the system may be turned off and then automatically move into an inactive mode unless an override switch 268 is activated. The alarm condition may also be depicted on an information/time display screen 270.

Alarm limits can be changed by the user if the set alarm limit does not suit the user. One or more algorithm tests are performed automatically, as with preprogrammed computer processing, to be sure that the limit is in fact a continuous or on-going problem. Eventually, if the problem persists and is not merely a transient condition, an alarm may be activated. The rate will not be permitted to go outside of the operating limits, both high and low limits will be imposed and maintained as the operating pressure prior to alarm. An override switch or button may be actuated to abort all limits and to allow the pump to be manually operated. Manual operation, in the preferred embodiment, will mean controlling the output flow rate of the pump by the operator directly through knob 166. Thus, the system is returned to a more traditional mode of operation by actuation of the override switch 268.

Information/time display screen 270 is advantageously included on or adjacent to the same face 140 of display 52. The information/time display screen 270 may include a large LED screen with multiple display fields, such as information display column 272 and 274. The information/time display screen 270 may also be provided in combination with a plurality of soft keys 276, 280, 284 and 288.

Soft key 276 is configured adjacent to, and informationally corresponds to, information field 278. Soft key 280 is correspondingly located adjacent to information field 282. Soft key 284 is adjacent to information field 286. Soft key 288 is adjacent to display field 290. Additional soft keys 291 and 292 are provided for use in connection with optional system configurations, the substance of which is beyond the scope of the present invention.

In the preferred embodiment, there are also designated function or mode keys provided in association with information display screen 270, such as a switch, key or button 293, for entering into a priming mode by which the system is primed with appropriate component solutions. A particular timer mode switch 294, a volume function switch 295, a calibration mode switch 296 and a defaults mode switch 297. The operation of controls, such as microprocessor 46 and various modes of operation will be described more fully below.

Generally, the primary modes of operation will advantageously include a "set-up" mode; a system priming mode; a run mode; a defaults mode; a timer mode; a volume function mode; and a calibration mode. The method of operator interaction with the inventive display panel and the controls associated with the control panel will be more fully described below.

When power is initially turned on, the display panel 52 and associated instrument controls 46 run internal diagnostic tests. While running the diagnostic tests, no switches, buttons or soft keys are activated by the operator unless there is an aspect of the tests which required attention from the operator. Preferably, the information/time display screen 270 will display the tests which are being performed as they are undertaken. Previously stored parameter values for the system, such as default values for the controllable characteristics of the cardioplegia delivery system will be displayed as appropriate. Any problems discovered will be displayed and preferably, the user will be prompted with appropriate instructions and/or inquiries for determining and/or affecting corrective procedures, if available.

Following initial power-up and testing, the display panel 52 and controls system 46 automatically enter an initial "set-up" mode. During the initial set-up mode, all of the digital displays which are preferably positioned along the displayed logical flow path 142 will display default values. Preferably, the default values are displayed in a relatively dim intensity. If a default value is zero, it is not displayed, and that parameter is skipped during set-up.

The information/time display screen 270 prompts the user to provide information by "asking" with an appropriate preprogrammed written question whether this is a new case. If it is a new case, the user presses one of the soft keys 276, 280, 288 or 284 in one of the display fields 278, 282, 286 or 290 which is positioned adjacent a "yes" appearing on the display screen 270. Alternatively, if it is a continuation of a case, the user is prompted to press another one of the soft keys adjacent to a "no" appearing in one of the display fields of the display screen 270.

If it is a new case (i.e., a different patient or medical operation) then set-up continues and a "change default" screen will appear in display screen 270 and the controls will be set to allow the user to change the default settings before continuing through set-up. Any zero default values which would not have been displayed during the set-up mode can be changed to a desired value. To change default settings, the user presses a soft key 280 corresponding to a "yes" response to an inquiry at screen 270 and enters the defaults mode. The default mode could alternatively be entered directly using default key 297.

If the existing default values are to be used, then the "no" response is entered via the soft key 284, which is depressed to continue with set-up.

In the set-up mode, a maximum retrograde pressure limit selection screen is presented at 270. The set legend light 158 comes on. The retrograde set switch 242 and LED light 243, (see FIG. 9) comes on. The maximum retrograde pressure limit value is displayed in upper limit display 234 in bright digits, preferably bright LED digits. The user changes the value with set knob 160. Pressing the ((retro set)) switch 242 confirms the selected value and the maximum retrograde pressure limit is displayed at 234 in dim LED digits.

The minimum retrograde pressure limit selection instructions on screen 270 comes on automatically in the initial set-up procedure. The set legend stays on from the previous step. The retrograde set LED 243 stays on. The minimum retrograde pressure limit value is displayed in bright LED digits at 238. The user changes the value with set knob 160. Pressing the retrograde set switch 242 confirms the value; the "retro set" LED light 243 goes off. The set legend light goes off and the minimum retrograde pressure is displayed in dim LED digits at 238.

Next in the initial set-up mode, a maximum antegrade pressure limit instruction may be displayed at screen 270. The set legend light 158 comes on. The "ante set" LED light 245 comes on, illuminating switch 244. A maximum antegrade pressure limit value is displayed, preferably with bright digits, such as LED digits, in upper limit display 234. The user changes the value with set knob 160. Pressing the antegrade set switch confirms the value and the maximum antegrade pressure is displayed in dim LED digits at 234.

Next, the minimum antegrade pressure limit selection screen is displayed in display screen 270. The set legend stays on from the previous step. The antegrade set LED light 245 also stays on. The minimum antegrade pressure limit value is now displayed in bright digits at the lower limit pressure display 238. The user changes the value with set knob 160. Pressing the antegrade set switch 244 confirms the value, turns off the "ante set" LED 245, turns off the set legend light 158 and the minimum antegrade pressure limit changes from a bright display to a dim display at lower limit display 238.

Next in the preferred embodiment of the present invention, a disposable cassette is used in the pump. A message may be displayed at screen 270 if the pump disposal cassette is not in place as detected by the instrument with a detection mechanism (not shown) after all the set-up parameters have been confirmed.

Next, an insert additive pouch screen message is displayed if an additive pouch is not in the instrument when all the set-up parameters have been confirmed.

An insert arrest agent pouch screen is displayed in display screen 270 an appropriate message if an arrest pouch (i.e., a container supplying the arrest agent) is not in the instrument when all the set-up parameters have been confirmed.

An insert heat exchanger screen is displayed in display screen 270 if the heat exchanger is not appropriately connected to the instrument when all the set-up parameters have been confirmed.

When the instrument has completed the set-up mode. All of the VF soft keys, all of the function keys and the control panel switches become operative. The instrument is ready to be primed. When priming is completed both with respect to the heat exchanger water and the various cardioplegia fluids, then the instrument moves into the run mode.

In the run mode, a run mode screen is displayed at 270. The run mode screen displays certain time dependent information useful to the perfusionist. For example, in the preferred embodiment, the primary run mode screen at 270 displays the delivery time which is preferably a cumulative delivery time for the particular patient. An off time is also displayed, which is preferably the off time since the last delivery of cardioplegia solution to the patient. Incremental volume of the cardioplegia solution delivered may be depicted and also a display indicating the remaining amounts of crystalloid, arrest agent and additive may be displayed. Preferably, an analog display of the remaining crystalloid, arrest agent and additive may be displayed to facilitate the user's quick understanding of the condition of the cardioplegia delivery system at a glance. When the delivery time is detected and accumulated based upon flow starting and flow stopping. The off time is also determined through detection of the flow stopping and flow starting. When delivery is started by turning the flow knob 166, the delivery time begins incrementing and accumulating. When the flow is stopped, as by turning flow control knob 166 so that the flow rate displayed at 164 is zero or if the system otherwise shuts down due to reaching excess limits or the like, then the delivery stops accumulating but remains displayed, the off time resets to zero and begins incrementing. When the flow is started again, the delivery time begins accumulating from the time previously displayed and the off time continues to be displayed. If delivery is interrupted again, then the off time resets to zero and begins incrementing and remains displayed when delivery is started again. Thus, the delivery time will represent a cumulative delivery time and the off time will be the duration of the most recent period of interrupted delivery. The off time incrementing does not begin until after the first delivery.

When the system is in the run mode, various messages may be displayed to notify the user of the system's inability to monitor antegrade flow rate limits or antegrade pressure limits, or alternatively, retrograde flow rate limits or retrograde pressure limits. Thus, screen 270 may provide a message to indicate that the flow rate limits cannot be monitored because of no transducer input available to the instrument. The user must supply a transducer and connect it to the system or zero the limits or the system will continue. If there is no transducer input available to the instrument, then an appropriate antegrade transducer/pressure limit message will be displayed at screen 270. The user must supply the pressure transducer input or zero the limits before the system will continue to operate in the run mode. Similarly, a retrograde/flow rate limit screen will be in display screen 270 if the flow rate limits cannot be monitored because no transducer input is available. The user must supply flow rate transducer input or zero the limits. A retrograde/flow rate pressure limit message may be presented at screen 270 if the limits cannot be monitored because no transducer input is available to the instrument. The user must supply the pressure transducer input or zero the limits. Zeroing the limits or requiring the transducer input is provided will avoid conditions where the operator is under a mistaken impression that upper and lower limits are being monitored by the instrument when no transducer input or inadequate transducer input is being provided so that the instrument can provide the limit monitoring functions.

The user enters and exits the defaults mode by pressing the defaults key 297 or enters during the set-up mode as previously discussed above.

When the instruments entered into a defaults mode, screen 270 prompts the user to select a parameter for which the default value is to be set or changed. The user selects the parameter to be changed by pressing the appropriate parameter switch on control panel 52. For example, parameter switch 242 allows defaults for the retrograde upper and lower flow limits; and parameter switch 244 allows antegrade upper and lower limits. Upon depressing one of the selected parameter switches, the selected switch light comes on and the digital displays display the default values in bright LED digits. The "set" legend light 158 comes on and the user can change or select the desired value using set knob 160. To confirm a new value, the user presses the parameter switch which toggles the switch to the off position, turns the switch light off, turns the set legend off, and changes the LED digits from a bright display to a dim display. After the user is through changing default values, he or she may exit and save the default values by pressing the save VF soft key 284. If the user wishes to return to the old default value before the updated defaults are saved, the user may press the undo VF soft key 280, which will restore the pre-updated default values and leaves the user in the default mode. If the user entered the defaults from the set-up mode, the user will return to the set-up mode. If the user wishes to exit the default mode, depressing the default function key 297 will leave the default mode. If the entered values have not been saved, the user will be prompted to save the new values or to undo the values before leaving the default mode. If the user entered the defaults mode from the set-up mode, the system will be returned to set-up. If the user entered the defaults mode from the run screen, the user will be returned to the run screen.

It can be seen that basically the same procedure for setting a desired value for any of the available adjustable characteristic parameters of the system can be accomplished substantially as described above with respect to the set-up mode. Upon saving or undoing the changes in the default values for the parameters and exiting the defaults mode with switch 297 returns the user to the point of entry, whether in the set-up mode or the run mode.

Other information screens and programmable aspects may be called up with the function keys. For example, by depressing the volume function key 295, screen 270 displays the total volume of cardioplegia solution delivered, the total blood volume delivered and the total crystalloid volume delivered. To reset the volume totals, the user depresses the soft key 284. To review the amount or dose of arrest agent or additive which have been delivered to the patient, the user depresses the review dose soft key 280. To re-set the totals, the re-set soft key 284 is depressed. To exit the volume mode, the volume function key 295 is depressed.

The user enters and exits a timer mode by pressing the timer function key 294. To exit the timer mode, the user presses the timer function key 294.

Throughout the operation of the inventive cardioplegia display and control various warning screens may be displayed. For example, when a flow limit first moves above or below a set level, a display may flash on screen 270 and no audible alarm is sounded. The flow limits will not be exceeded but the desired pressure will change. After a period of time if the condition is not corrected or overridden, for a period of time an audible alarm may be sounded. If the override button is activated, or if automatic pressure switch is toggled, then the system moves into the volume control mode. Knob 166 is activated.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A method for establishing constant pressure blood mixture fluid delivery to a patient comprising the steps of:
   (a) connecting a fluid delivery tube between the patient and an adjustable rate pump of a type for pumping blood mixture fluid at an adjustable flow rate;
   (b) increasing the rate of pumping of fluid to the patient through the tube;
   (c) measuring pressure in the fluid delivery tube while increasing the flow rate there through; and
   (d) upon measuring a desired pressure, simultaneously disengaging a manual flow rate adjustment mechanism and engaging an automatic control mechanism by which the flow rate in said fluid delivery tube is automatically adjusted to maintain said desired pressure.

2. A system for blood mixture fluid delivery to a vascular system of a patient comprising:
   (a) a fluid delivery conduit connectable to said vascular system of the patient for delivering a blood mixture fluid;
   (b) a pump interconnected to said fluid delivery conduit for controlled pumping of said blood mixture fluid through said conduit to said vascular system of the patient; and
   (c) a control mechanism operatively connected to said pump for controlling a rate at which fluid is pumped from said pump so that said blood mixture fluid is delivered to said vascular system of the patient at a defined and maintained constant pressure.

3. A system for blood mixture fluid delivery as in claim 2 wherein said fluid delivery conduit is an arterial conduit for coupling said delivery system to said patient's arterial blood vessel system.

4. A system for blood mixture fluid delivery as in claim 2 wherein said fluid delivery conduit is a venous conduit for coupling said delivery system to said patient's venous blood vessel system.

5. A system for blood mixture fluid delivery as in claim 2 wherein;
   (a) said pump has a variable flow rate within a predetermined range of flow rates; and
   (b) wherein said control mechanism, for controlling said rate at which fluid is pumped from said pump, automatically controls and maintains fluid delivery at said defined constant pressure and includes:
      i. a pressure sensor operatively connected with said fluid delivery conduit for detecting a blood mixture fluid delivery pressure to said vascular system of the patient and for producing a representative signal of said detected pressure; and
      ii. control circuitry for receiving said representative pressure signal and for automatically increasing said variable flow rate upon detecting a pressure below said defined constant pressure, for automatically decreasing said variable flow rate upon detecting a pressure above said defined constant pressure and for automatically holding said flow rate constant upon detecting a pressure equal to said defined constant pressure so that said blood mixture fluid is delivered to said vascular system of the patient at said defined constant pressure.

6. A system for blood mixture fluid delivery as in claim 2 further comprising:
   (a) a fluid path in said system which includes said fluid delivery conduit and said pump;
   (b) a pressure display, coupled to said control mechanism, by which said defined and maintained constant delivery pressure is displayed; and
   (c) a flow rate display, coupled to said control mechanism, which displays an actual fluid flow rate measured along said fluid path in said system, such actual fluid flow rate being proportional to said defined constant pressure.

7. A system for blood mixture fluid delivery as in claim 6 further comprising:
   (a) a flow rate adjustment device coupled to said control mechanism; and
   (b) a switch, coupled to said control mechanism, for changing between a flow rate control mode and a constant pressure control mode whereby,
      (i) in said flow rate control mode, said actual fluid flow rate is changed by manually adjusting said flow rate adjustment device, and
      (ii) in said constant pressure control mode, by which said flow rate adjustment device is deactivated, said control mechanism is enabled to automatically maintain a fluid delivery pressure substantially consistent with said defined constant pressure through automatic adjustment of the actual fluid flow rate.

8. A system for blood mixture fluid delivery as in claim 7 further comprising:
   (a) means, coupled to said control mechanism, for defining an upper pressure limit; and
   (b) means, coupled to said control mechanism, for defining a lower pressure limit.

9. A system for blood mixture fluid delivery as in claim 8 further comprising means, coupled to said control mechanism, for defining an upper flow rate limit and for defining a lower flow rate limit based upon said upper pressure limit and said lower pressure limit, respectively, said actual fluid flow rate and an actual fluid pressure, such actual flow rate and actual fluid pressure being determined upon activation of said constant pressure control mode.

10. A system for blood mixture fluid delivery as in claim 9 further comprising:
   (a) a monitoring means within said fluid path;
   (b) a first alarm, being coupled to said monitoring means within said fluid path, to operatively monitor said actual fluid flow rate, to provide a first signal if said actual fluid flow rate exceeds said upper flow rate limit or falls below said lower flow rate limit;
   (c) a second alarm, being coupled to said monitoring means within said fluid path, to monitor said actual fluid flow rate, to provide a second signal if said actual fluid flow rate exceeds said upper flow rate limit for a first predetermined period of time or said actual flow rate falls below said lower flow rate limit for a second predetermined period of time;
   (d) an automatic shut-off switch, coupled to said control mechanism, by which said pump will be deactivated if said actual fluid flow rate exceeds said upper flow rate limit for a third predetermined period of time after said second signal has occurred or if said actual fluid flow rate falls below said lower flow rate limit for a fourth predetermined period of time after said second alarm has occurred; and
   (e) an operator override switch, coupled to said control mechanism, by which said at least one of said first and second signals can be manually overridden by an operator to discontinue at least one of the signals and continue operation of the pump even when said upper and lower flow rate limits are exceeded.

11. A system for blood mixture fluid delivery as in claim 8 further comprising:
   (a) computer processing circuitry, operatively connected to said control mechanism, for automatically calculating upper and lower flow rate limits based upon upper and lower pressure limits set with said means for setting upper and lower pressure limits; and
   (b) means, coupled to said computer processing circuitry, for automatically setting said upper and lower flow rate limits based upon said calculated upper and lower flow rate limits upon actuation of said constant pressure control mode.

12. A system for blood mixture fluid delivery as in claim 2 further comprising:
   (a) means for setting upper pressure and lower pressure limits, said means operatively connected to said system for blood mixture fluid delivery; and
   (b) means, coupled to said control mechanism, for automatically establishing an upper flow rate limit and a lower flow rate limit based upon set upper pressure and lower pressure limits.

13. A system for blood mixture fluid delivery as in claim 12 further comprising:
   (a) a fluid path through said system;
   (b) a monitoring means for monitoring actual pressure within said fluid path;
   (c) a first alarm, being coupled to said monitoring means within said fluid path through said system to operatively monitor an actual fluid flow rate, to provide a visual signal if said actual fluid flow rate exceeds said upper flow rate limit or falls below said lower flow rate limit;
   (d) a second alarm, being coupled to said monitoring means within said fluid path, to monitor said actual flow rate, to provide an audible signal if said actual fluid flow rate exceeds said upper flow rate limit for a first predetermined period of time or said actual fluid flow rate falls below said lower flow rate limit for a second predetermined period of time;
   (e) an automatic shut-off switch, coupled to said control mechanism, by which said pump will be deactivated if said actual fluid flow rate exceeds said upper flow rate limit for a third predetermined period of time after said audible signal has occurred or if said actual fluid flow rate falls below said lower flow rate limit for a fourth predetermined period of time after said audible signal has occurred; and
   (f) an operator override switch, coupled to said control mechanism, by which said automatic shut-off switch and at least one of said visual and audible alarms can be manually overridden by an operator to discontinue at least one of the signals to continue operation of the pump even when said upper and lower flow rate limits are exceeded.

14. A system for blood mixture fluid delivery as in claim 12 further comprising:
   (a) a fluid path through said system;
   (b) a monitoring means for monitoring actual pressure within said fluid path;
   (c) a first alarm, being coupled to said monitoring means within said fluid path through said system to operatively monitor an actual fluid pressure within said fluid path, to provide a visual signal if said actual fluid pressure exceeds said upper pressure limit or falls below said lower pressure limit;
   (d) a second alarm, being coupled to said monitoring means within said fluid path to monitor said actual fluid pressure, to provide an audible signal when said actual fluid pressure exceeds said upper pressure limit for a first predetermined period of time or said actual fluid pressure falls below said lower pressure limit for a second predetermined period of time; and
   (e) an operator override switch, coupled to said control mechanism, by which at least one of said visual and said audible signals can be manually overridden by an operator to discontinue at least one of the alarms to continue operation of the pump even when said upper and lower pressure limits are exceeded.

15. A system for blood mixture fluid delivery as in claim 2 wherein said system is a cardioplegia delivery system.

16. A system for blood mixture fluid delivery as in claim 2 wherein said system is a limb reperfusion system.

17. A system for blood mixture fluid delivery as in claim 2 wherein said system is a cerebral perfusion system.

18. A system for blood mixture fluid delivery to a patient comprising:
   (a) fluid delivery conduits connectable to said patient for delivering a blood mixture fluid wherein said fluid delivery conduits are operatively positioned within said patient's arterial vascular system and said patient's venous vascular system, and operatively connected to said system for blood mixture fluid delivery for selectable delivery to either said arterial system or to said venous system of said patient;
   (b) a pump interconnected to said fluid delivery conduits for controlled pumping of said blood mixture fluid through said conduits to the patient; and
   (c) a control mechanism operatively connected to said pump for controlling said pump so that said blood mixture fluid is delivered to the patient at a defined constant pressure.

19. A system for blood mixture fluid delivery to a patient comprising:
   (a) a fluid delivery conduit connectable to said patient for delivering a blood mixture fluid;
   (b) a pump, having an adjustably variable flow rate and interconnected to said fluid delivery conduit, for controlled pumping of said blood mixture fluid through said conduit to the patient; and
   (c) a control mechanism operatively connected to said pump for controlling said pump so that said blood mixture fluid is delivered to the patient at a defined constant pressure, said control mechanism including:
      i. means for manually adjusting a variable flow rate;
      ii. means for automatically controlling said variable flow rate to maintain said defined constant pressure; and
      iii. means for selecting between said manual flow rate control and said automatic flow rate control for maintaining said defined constant pressure.

20. A system for blood mixture fluid delivery as in claim 19 wherein said means for selecting between said manual and said automatic control comprises a mode selection switch having (i) a first position, in which said means for manually adjusting said variable flow rate is activated, and (ii) a second position, in which said means for automatically controlling said variable flow rate to maintain said defined constant pressure is activated.

21. A system for blood mixture fluid delivery to a vascular system of a patient at a constant pressure comprising:
   (a) means for selecting a defined constant pressure;

(b) pump means for delivering a blood mixture fluid under pressure to said vascular system of the patient;

(c) a monitor for measuring pressure of said blood mixture fluid delivered to said vascular system of the patient and for providing a signal representative of said measured pressure; and (d) control means, coupled between said means for selecting a defined constant pressure, said pump means and said monitor means, responsive to said signal representative of said measured pressure for controlling the rate at which fluid is pumped by said pump means so that said blood mixture fluid is delivered and maintained at said defined constant pressure.

22. A system for blood mixture fluid delivery to a vascular system of a patient at a constant pressure, wherein said delivery system comprises:

(a) means for controlling a variable blood mixture fluid flow rate in said delivery system;

(b) a control mechanism operatively associated with said means for controlling a variable blood mixture fluid flow rate for maintaining said constant pressure by controlling said variable blood mixture fluid flow rate;

(c) means, coupled to said control mechanism, to allow initial adjustment of said variable blood mixture fluid flow rate until a defined fluid delivery pressure is achieved, such defined fluid delivery pressure corresponding to a defined constant pressure; and (d) means, coupled to said control mechanism, to allow changing an operation mode of the delivery system to a constant pressure mode whereby in said constant pressure mode said variable blood mixture fluid flow rate is automatically varied so that said fluid delivery pressure is constantly maintained at said defined constant pressure.

23. A system for blood mixture fluid delivery to a patient comprising:

(a) fluid delivery conduit, operatively positioned within said patient at a delivery situs, for delivering a blood mixture fluid to said delivery situs;

(b) a pump, coupled to said fluid delivery conduit, for producing a pressurized flow of said blood mixture fluid through said conduit to the patient;

(c) a control mechanism, coupled to said pump, having a first manual flow rate control mode and having a second automatic constant pressure control mode operatively connected to said pump; and (d) means, coupled to said control mechanism, for selectably choosing said manual flow rate control mode or said automatic constant pressure control mode.

24. A system for blood mixture fluid delivery as in claim 23 further comprising means, coupled to said control mechanism, for providing a measurement of a fluid flow rate in said system at the time of selectably choosing said automatic constant pressure control mode and for automatically setting high and low flow rate limits using an algorithm based upon a measurement of a fluid flow rate in said system at the time of selectably choosing said automatic constant pressure control mode.

25. A system for blood mixture fluid delivery as in claim 23 further comprising means, coupled to said control mechanism, for manually selecting high and low flow rate limits for said automatic constant pressure control mode.

26. A system for blood mixture fluid delivery as in claim 23 further comprising a display panel, coupled to said control mechanism, having:

(a) a means for selecting between said manual flow rate control mode and said automatic constant pressure control mode;

(b) a first flow rate measurement and visual display device for measuring and displaying a measured fluid flow rate; and (c) a second pressure measurement and visual display device for measuring and displaying a measured fluid pressure.

27. A system for blood mixture fluid delivery as in claim 26 further comprises:

(a) an upper limit display area on said display panel;

(b) a lower limit display area on said display panel;

(c) means for defining an upper pressure limit to be displayed in said upper limit display area; and (d) means for defining a lower pressure limit for display in said lower limit display area.

28. A system for blood mixture fluid delivery as in claim 27 further comprises:

means operatively connected with said means for selecting between said automatic manual control mode and said automatic constant control mode for automatically defining upper and lower flow rate limits based upon displayed upper and lower pressure limits and for automatically replacing said upper and lower pressure limits with said automatically defined upper and lower flow rate limits for display in said upper and lower limit display areas.

29. A system for blood mixture fluid delivery as in claim 28 wherein, (a) said display panel further includes,
 (i) a first display area for visually designating said upper and said lower display areas for pressure limit display;
 (ii) a second display area for visually designating said upper and said lower limit display areas for flow rate limit display; and (b) said control means further includes means for blanking out said pressure limit designation upon activation of said automatic constant pressure control mode and eliminating said pressure limit display, or alternatively for blanking said flow rate limit designation display and for elimination of said flow rate limit display upon deactivation of said automatic constant pressure control mode and reactivation of said manual flow rate adjustment mode.

* * * * *